(12) United States Patent
Maltz et al.

(10) Patent No.: US 11,841,104 B2
(45) Date of Patent: Dec. 12, 2023

(54) SYSTEM AND METHOD FOR EQUALIZING PRESSURE IN IONIZATION CHAMBER OF RADIATION DEVICE

(71) Applicant: SHANGHAI UNITED IMAGING HEALTHCARE CO., LTD., Shanghai (CN)

(72) Inventors: Jonathan Maltz, Houston, TX (US); Johannes Stahl, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 537 days.

(21) Appl. No.: 16/854,821

(22) Filed: Apr. 21, 2020

(65) Prior Publication Data
US 2021/0325917 A1    Oct. 21, 2021

(51) Int. Cl.
*F16L 51/00*    (2006.01)
*G05D 16/20*    (2006.01)
(Continued)

(52) U.S. Cl.
CPC ............ *F16L 51/00* (2013.01); *A61B 6/44* (2013.01); *A61B 6/54* (2013.01); *F16L 51/02* (2013.01);
(Continued)

(58) Field of Classification Search
CPC . G05D 16/2066; G05D 16/2013; H01J 47/02; G01T 1/02; G01T 1/185;
(Continued)

(56) References Cited

U.S. PATENT DOCUMENTS 1,669,183 A * 5/1928 Wilson ............... F17B 1/24
220/721
1,681,676 A * 8/1928 Moore ............... F17B 1/02
220/721

(Continued)

FOREIGN PATENT DOCUMENTS

CN    101526623 A    9/2009
CN    104319222 A    1/2015
(Continued)

OTHER PUBLICATIONS

Romeo Calin, Gas Spherical Ionization Chamber, Journal of Radioanalytical and Nuclear Chemistry, 290: 361-366, 2011.
(Continued)

*Primary Examiner* — William M McCalister
(74) *Attorney, Agent, or Firm* — METIS IP LLC

(57) ABSTRACT

A system for equalizing a pressure in an ionization chamber of a radiation device is provided. The system may include the ionization chamber including: a chamber housing including one or more chamber walls; a chamber volume inside the chamber housing, the chamber volume being filled with a radiation sensitive material; and a pressure adjustment apparatus operably coupled to the chamber volume via at least one wall of the one or more chamber walls, the pressure adjustment apparatus being configured to equalize a first pressure of the radiation sensitive material inside the chamber volume and a second pressure of ambient air outside the chamber housing.

11 Claims, 14 Drawing Sheets

(51) Int. Cl.
*H01J 47/02* (2006.01)
*F16L 51/02* (2006.01)
*G01T 1/185* (2006.01)
*A61B 6/00* (2006.01)
*G01T 1/02* (2006.01)
*A61N 5/10* (2006.01)

(52) U.S. Cl.
CPC ......... *G01T 1/185* (2013.01); *G05D 16/2013* (2013.01); *G05D 16/2066* (2013.01); *H01J 47/02* (2013.01); *A61N 5/1071* (2013.01); *G01T 1/02* (2013.01)

(58) Field of Classification Search
CPC .. F16L 51/00; F16L 51/02; A61B 6/44; A61B 6/54; A61N 5/1071
USPC .......................................... 220/720, 721, 722
See application file for complete search history.

(56) References Cited

U.S. PATENT DOCUMENTS

| | | | | |
|---|---|---|---|---|
| 1,726,281 | A * | 8/1929 | Wilson | F17B 1/24 220/721 |
| 2,111,839 | A * | 3/1938 | Chenicek | F17B 1/02 48/178 |
| 3,494,274 | A * | 2/1970 | Evers | B65D 90/30 220/721 |
| 3,510,319 | A * | 5/1970 | Whitaker | A01F 25/08 220/721 |
| 3,528,360 | A * | 9/1970 | Broberg | A01F 25/16 99/476 |
| 4,129,069 | A * | 12/1978 | Thompson | A23L 3/3418 138/30 |
| 4,135,443 | A * | 1/1979 | Warren | A01F 25/163 220/721 |
| 4,195,668 | A * | 4/1980 | Lewis | F16L 55/053 220/721 |
| 4,321,866 | A * | 3/1982 | Thompson | A01F 25/163 220/722 |
| 4,367,409 | A | 1/1983 | Klausz | |
| 4,375,784 | A * | 3/1983 | Kalnins | A01F 25/163 220/721 |
| 4,379,248 | A | 4/1983 | Wakayama et al. | |
| 4,434,712 | A * | 3/1984 | Ross | A01F 25/163 220/721 |
| 4,695,731 | A | 9/1987 | Larkin | |
| 4,873,445 | A * | 10/1989 | Le Jeune | H01J 37/08 118/723 R |
| 5,434,748 | A * | 7/1995 | Fukui | H05K 5/068 174/559 |
| 5,672,878 | A | 9/1997 | Yao | |
| 5,796,110 | A | 8/1998 | An et al. | |
| 6,220,474 | B1 * | 4/2001 | Bedon | B65D 83/0061 220/666 |
| 6,221,312 | B1 | 4/2001 | Van Laar et al. | |
| 7,108,015 | B2 * | 9/2006 | Lombari | F24D 3/1041 220/721 |
| 7,621,296 | B2 * | 11/2009 | Freissler | F16L 55/053 138/104 |
| 8,820,551 | B2 * | 9/2014 | Arney | B65D 53/00 220/232 |
| 2005/0017016 | A1 * | 1/2005 | Lombari | F24D 3/1016 220/721 |
| 2012/0181442 | A1 | 7/2012 | Prieels | |
| 2014/0125349 | A1 | 5/2014 | Mccormick | |
| 2014/0265823 | A1 * | 9/2014 | Boisseau | H01J 47/02 313/621 |
| 2019/0254621 | A1 * | 8/2019 | Komasaka | A61B 6/4233 |

FOREIGN PATENT DOCUMENTS

| | | |
|---|---|---|
| CN | 210224598 U | 3/2020 |
| GB | 814890 A | 6/1959 |
| GB | 887148 A | 1/1962 |
| GB | 900428 A | 7/1962 |
| TW | 562854 B | 11/2003 |

OTHER PUBLICATIONS

Hugo Bouchard et al., Ionization Chamber-Based Reference Dosimetry of Intensity Modulated Radiation Beams, Medical Physics, 31(9): 2454-2465, 2004.

K R Shortt et al., The Effect of Wall Thickness on the Response of a Spherical Ionization Chamber, Physics in Medicine and Biology, 47(10): 1721-1731, 2002.

B. Shumard et al., Transmission Ion Chamber: Design and Application, Nuclear Instruments and Methods in Physics Research Section B, 241: 446-449, 2005.

L. V. Vladimirov et al., Transmission-Type Ionization Chamber for Monitoring Dose Power of an X-Ray Therapeutic Apparatus, Biomedical Engineering, 46(2): 50-52, 2012.

J Wulff et al., Monte-Carlo-Based Perturbation and Beam Quality Correction Factors for Thimble Ionization Chambers in High-Energy Photon Beams, Physics in Medicine and Biology, 53(11): 2823-2836, 2008.

* cited by examiner

800

From/To Chamber

SYSTEM AND METHOD FOR EQUALIZING PRESSURE IN IONIZATION CHAMBER OF RADIATION DEVICE

TECHNICAL FIELD

The present disclosure generally relates to a radiation device, and more specifically relates to systems and methods for equalizing a pressure in an ionization chamber of a radiation device.

BACKGROUND

Radiation beams are widely used in imaging devices and/or treatment devices. However, radiation beams of high radiation intensity may cause a serious damage to healthy organs or tissues. Therefore, it is desirable to monitor or detect the intensity of the radiation beams. An ionization chamber is commonly used to monitor or detect the intensity of radiation beams. An ionization chamber can be sealed or unsealed. An unsealed ionization chamber may be equipped with one or more small vents to allow equalization between a pressure inside the ionization chamber and a pressure of ambient air. However, an unsealed ionization chamber often needs to be compensated for temperature and/or pressure variations, and can be influenced by moisture in the ambient air. A sealed ionization chamber does not exchange radiation sensitive materials (e.g., air) with the ambient air, and usually does not have the problems of the sealed ionization chamber. However, the pressure inside the sealed ionization chamber and the pressure of the ambient air can be different, and the pressure difference between the interior and exterior of the chamber may distort the walls and/or plates of the sealed ionization chamber. To this end, a relatively thick chamber wall needs to be used for the sealed ionization chamber. Because thicker walls can attenuate and scatter radiation beams to a greater extent than thinner walls, the performance of a sealed ionization chamber in electron radiation dosimetry or lower energy photon dosimetry can be negatively affected. Therefore, it is desirable to provide methods and systems for equalizing the pressure in a thin-walled ionization chamber without allowing ingress of the ambient air.

SUMMARY

According to a first aspect of the present disclosure, a system for equalizing a pressure in an ionization chamber of a radiation device is provided. The system may include the ionization chamber including: a chamber housing including one or more chamber walls; a chamber volume inside the chamber housing, the chamber volume being filled with a radiation sensitive material; and a pressure adjustment apparatus operably coupled to the chamber volume via at least one wall of the one or more chamber walls, the pressure adjustment apparatus being configured to equalize a first pressure of the radiation sensitive material inside the chamber volume and a second pressure of ambient air outside the chamber housing.

In some embodiments, the chamber volume may be airtight.

In some embodiments, the at least one wall may have a thickness between 10 micrometers and 2 millimeters.

In some embodiments, the radiation sensitive material may include a gas.

In some embodiments, the gas may include atmospheric air.

In some embodiments, the pressure adjustment apparatus may include: a tube including a first end and a second end, the first end being open to the chamber volume through the at least one wall, and the second end being open to the ambient air; and a fluid material trapped inside the tube, the fluid material being configured to move within the tube to equalize the first pressure and the second pressure.

In some embodiments, the at least one wall may include a hole, and the first end of the tube may be airtightly connected to the at least one wall via the hole.

In some embodiments, the first end of the tube may be directly connected to the at least one wall.

In some embodiments, the first end of the tube may be connected to the at least one wall through a connecting piece.

In some embodiments, at least a portion of the tube may include a capillary, and the fluid material may be trapped in the capillary.

In some embodiments, at least a portion of the tube may include two or more capillaries in parallel, and the fluid material may be trapped in each of the two or more capillaries.

In some embodiments, a space between the first end of the tube and the fluid material may be at least partially filled with the radiation sensitive material, and the space may be in fluid communication with the chamber volume.

In some embodiments, the fluid material may be further configured to form an airtight seal within the tube that isolates the radiation sensitive material from the ambient air.

In some embodiments, the fluid material may be further configured to form an airtight seal within the tube that prevents the ambient air from affecting a humidity of the chamber volume.

In some embodiments, the fluid material may be further configured to prevent the ambient air from affecting a temperature of the radiation sensitive material.

In some embodiments, the fluid material may be hydrophobic.

In some embodiments, the fluid material may include an oil.

In some embodiments, the pressure adjustment apparatus may include: an enclosure configured to function as a reservoir of the radiation sensitive material; and a tube including a first end and a second end, the first end being open to the chamber volume, and the second end being open to the enclosure.

In some embodiments, the at least one wall may include a hole, and the first end of the tube may be airtightly connected to the at least one wall via the hole.

In some embodiments, the first end of the tube may be directly connected to the at least one wall.

In some embodiments, the first end of the tube may be connected to the at least one wall through a connecting piece.

In some embodiments, the enclosure may be in fluid communication with the chamber volume through the tube.

In some embodiments, the enclosure and the tube may be airtight such that the radiation sensitive material inside the enclosure and the tube may be isolated from the ambient air.

In some embodiments, the enclosure may be flexible.

In some embodiments, the enclosure may include a balloon, a bellows, or a flexible enclosure.

In some embodiments, the enclosure may be made of a first material having a first elastic modulus, the one or more chamber walls may be made of one or more second materials each having a second elastic modulus, and the first elastic modulus may be lower than the second elastic modulus.

In some embodiments, the pressure adjustment apparatus may include: an enclosure configured to function as a reservoir of the radiation sensitive material; and a pump configured to pump, based on the first pressure and the second pressure, the radiation sensitive material to flow between the enclosure and the chamber volume.

In some embodiments, the enclosure may be in fluid communication with the chamber volume via a tube.

In some embodiments, the enclosure and the tube may be airtight such that the radiation sensitive material inside the enclosure and the tube may be isolated from the ambient air.

In some embodiments, the pressure adjustment apparatus may further include: a first pressure sensor configured to detect the first pressure; and a second pressure sensor configured to detect the second pressure.

In some embodiments, the pressure adjustment apparatus may include: an enclosure configured to function as a reservoir of the radiation sensitive material; a tube configured to guide the radiation sensitive material to flow into and out of the chamber volume; and a pump configured to pump, based on the first pressure and the second pressure, the radiation sensitive material to flow between the enclosure and the chamber volume via the tube; and pump the radiation sensitive material to flow between the chamber volume and the tube.

In some embodiments, the pressure adjustment apparatus may further include: a first pressure sensor configured to detect the first pressure by detecting a pressure of the radiation sensitive material flowing through the tube; and a second pressure sensor configured to detect the second pressure.

In some embodiments, the first pressure sensor may be operably coupled to the tube.

In some embodiments, the pressure adjustment apparatus may further include: a thermometer configured to detect a temperature of the radiation sensitive material inside the chamber volume by detecting a temperature of the radiation sensitive material flowing through the tube.

In some embodiments, the temperature sensor may be operably coupled to the tube.

In some embodiments, the pressure adjustment apparatus may further include: a proportional valve configured to adjust a quantity of the radiation sensitive material flowing, through the tube, in or out of the chamber volume.

In some embodiments, the tube may include a first end and a second end, the first end being connected to a first location of the chamber housing, and the second end being connected to a second location of the chamber housing.

In some embodiments, the enclosure may be operably connected to the tube and in fluid communication with the tube.

In some embodiments, the enclosure and the tube may be airtight such that the radiation sensitive material inside the enclosure and the tube may be isolated from the ambient air.

In some embodiments, the ionization chamber may further include: one or more electrodes configured to establish an electric field in the chamber volume and measure a charge or current associated with the radiation sensitive material and produced, based on the electric field, in the chamber volume.

In some embodiments, the pressure adjustment apparatus may include: an enclosure configured to function as a reservoir of the radiation sensitive material; and a pressure regulating element separating the enclosure into a first space and a second space, the first space being in fluid communication with the chamber volume via a tube, the second space being in fluid communication with the ambient air.

In some embodiments, the pressure regulating element may be configured to equalize the first pressure and the second pressure by regulating a first size of the first space and a second size of the second space.

In some embodiments, the pressure regulating element may be a flexible membrane, a moveable membrane, a plunger, or a concertina.

According to a second aspect of the present disclosure, a method for equalizing a pressure of a radiation sensitive material in an ionization chamber is provided. The method may include: providing an ionization chamber, wherein the ionization chamber includes a chamber housing including one or more chamber walls; a chamber volume inside the chamber housing, the chamber volume being filled with a radiation sensitive material; and a pressure adjustment apparatus operably coupled to at least one wall of the one or more chamber walls, the pressure adjustment apparatus being configured to equalize a first pressure of the radiation sensitive material inside the chamber volume and a second pressure of ambient air outside the chamber housing; detecting the first pressure of the radiation sensitive material inside the ionization chamber; detecting the second pressure of the ambient air outside the ionization chamber; and equalizing the first pressure and the second pressure by pumping, using a pump and based on the first pressure and the second pressure, the radiation sensitive material to flow between a reservoir of the radiation sensitive material and the ionization chamber.

In some embodiments, the equalizing the first pressure and the second pressure may include: comparing the first pressure and the second pressure; and in response to a determination that the first pressure is larger than the second pressure, pumping the radiation sensitive material from the ionization chamber to the reservoir.

In some embodiments, the equalizing the first pressure and the second pressure may include: comparing the first pressure and the second pressure; and in response to a determination that the second pressure is larger than the first pressure, pumping the radiation sensitive material from the reservoir to the ionization chamber.

In some embodiments, the method may further include: allowing the radiation sensitive material to flow between an ionization chamber and a tube operably coupled to the ionization chamber.

In some embodiments, the detecting the first pressure of the radiation sensitive material inside the ionization chamber may include: detecting the first pressure of the radiation sensitive material inside the ionization chamber by detecting a pressure of the radiation sensitive material flowing through the tube.

In some embodiments, the causing the radiation sensitive material to flow may include: pumping continuously the radiation sensitive material inside the tube into the ionization chamber; and/or pumping continuously the radiation sensitive material from the ionization chamber into the tube.

In some embodiments, the method may further include: comparing the first pressure and the second pressure; and in response to a determination that the first pressure is different from the second pressure and that a pumping direction of the pump is irreversible, adjusting a proportional valve to equalize the first pressure and the second pressure.

In some embodiments, the method may further include: comparing the first pressure and the second pressure; comparing a pump speed of the pump and a threshold; and in response to a determination that the first pressure is different from the second pressure and that the pump speed of the pump is no less than the threshold, adjusting a proportional valve to equalize the first pressure and the second pressure.

According to a third aspect of the present disclosure, a non-transitory computer readable medium may include at least one set of instructions for equalizing a pressure of a radiation sensitive material in an ionization chamber. The at least one set of instructions may be executed by one or more processors of a computer device. The one or more processors may provide an ionization chamber, wherein the ionization chamber includes a chamber housing including one or more chamber walls; a chamber volume inside the chamber housing, the chamber volume being filled with a radiation sensitive material; and a pressure adjustment apparatus operably coupled to at least one wall of the one or more chamber walls, the pressure adjustment apparatus being configured to equalize a first pressure of the radiation sensitive material inside the chamber volume and a second pressure of ambient air outside the chamber housing. The one or more processors may detect the first pressure of the radiation sensitive material inside the ionization chamber. The one or more processors may detect the second pressure of the ambient air outside the ionization chamber. The one or more processors may equalize the first pressure and the second pressure by pumping, using a pump and based on the first pressure and the second pressure, the radiation sensitive material to flow between a reservoir of the radiation sensitive material and the ionization chamber.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, sections or assembly of different levels in ascending order.

However, the terms may be displaced by another expression if they achieve the same purpose.

Figure 2:
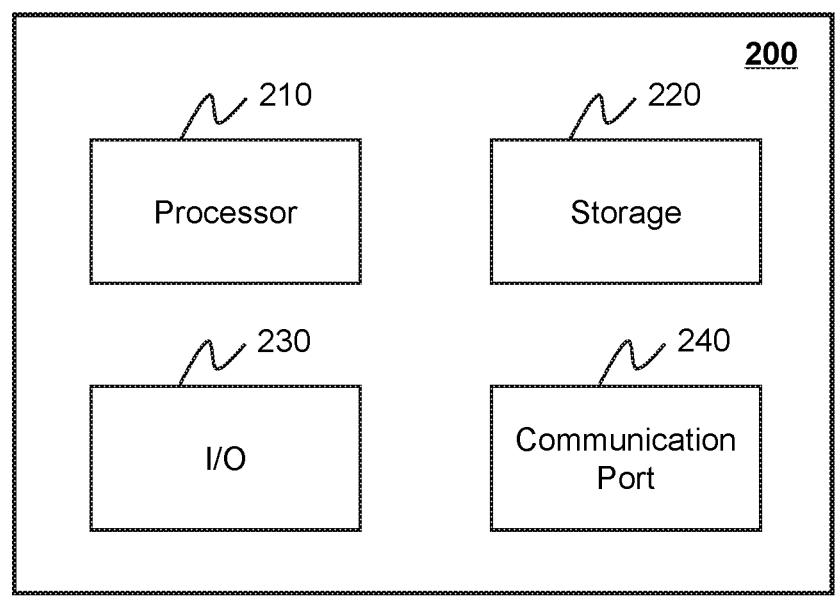
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Radiation systems (e.g., radiation therapy systems, radiation imaging systems) may include a dosimetry module in order to measure and/or regulate radiation output (e.g., the intensity of radiation beams). Two types of ionization chambers may be used as the dosimetry module, for example, a sealed ionization chamber, an unsealed ionization chamber. A sealed ionization chamber may have a sealed wall that prevents ingress or egress of the ambient air, while an unsealed ionization chamber may have an unsealed wall and allow ingress and/or egress of the ambient air. The unsealed ionization chamber may be equipped with one or more vents to allow pressure equalization between the ionization chamber and the ambient air, and accordingly a pressure difference therebetween may be eliminated. However, the unsealed ionization chamber may need to be compensated for temperature and/or pressure variations, and may be influenced by moisture in the ambient air. In some embodiments, desiccants may be used to absorb moisture in the ambient air before the ambient air enters the chamber. In some embodiments, the chamber may be heated to inhibit moisture condensation and/or aid moisture evaporation. This may make the configuration and/or usage of the unsealed ionization chamber complex and inconvenient. These problems may be solved by using the sealed ionization chamber. However, the pressure inside the sealed ionization chamber and the pressure of the ambient air may be different, and the pressure difference therebetween may distort the walls and plates of the sealed ionization chamber. The distortion may affect the calibration of the sealed ionization chamber and/or bias the measurements of the radiation beams. To this end, a relatively thick chamber wall may be used for the sealed ionization chamber. However, the relatively thick chamber wall may attenuate and/or scatter the radiation beams, and the sealed ionization chamber with the relatively thick chamber wall may be unsuitable for electron radiation dosimetry or lower energy photon dosimetry.

The present disclosure relates to systems and methods for equalizing a pressure of a radiation sensitive material in an ionization chamber, which may provide a hybrid of a sealed and unsealed ionization chamber in which the pressure inside the chamber may be actively or passively equalized relative to the pressure of the ambient air, without allowing ingress and/or egress of the ambient air. In some embodiments, an ionization chamber may be provided with a pressure adjustment apparatus. For example, the ionization chamber may include a chamber housing including one or more chamber walls, a chamber volume inside the chamber housing, and a pressure adjustment apparatus operably coupled to at least one wall of the one or more chamber walls. In some embodiments, a first pressure of a radiation sensitive material inside the ionization chamber and a second pressure of the ambient air outside the ionization chamber may be equalized actively or passively by the pressure adjustment apparatus. For example, the first pressure and the second pressure may be equalized by pumping, using a pump and based on the first pressure and the second pressure, the radiation sensitive material to flow between a reservoir of the radiation sensitive material and the ionization chamber. The radiation sensitive material may refer to any substance (e.g., a gas, a liquid, etc.) that can be used in the ionization chamber to monitor or detect the intensity of radiation beams. For instance, the air may be used as a radiation sensitive material filling the ionization chamber. Any ionizable material may be used as a radiation sensitive material filling the ionization chamber. A hybrid of the sealed and unsealed ionization chamber of the present disclosure may have a relatively thin chamber wall, which may facilitate the detection of radiation beams by lowering the amount of attenuation experienced by the beam(s) due to transit through the chamber assembly. Besides, the hybrid of the sealed and unsealed ionization chamber of the present disclosure may avoid air exchange with the ambient air, and accordingly, temperature compensation and/or pressure compensation may be unnecessary, and an effect on the performance of the ionization chamber due to moisture in the ambient air may be avoided or reduced.

Figure 1:
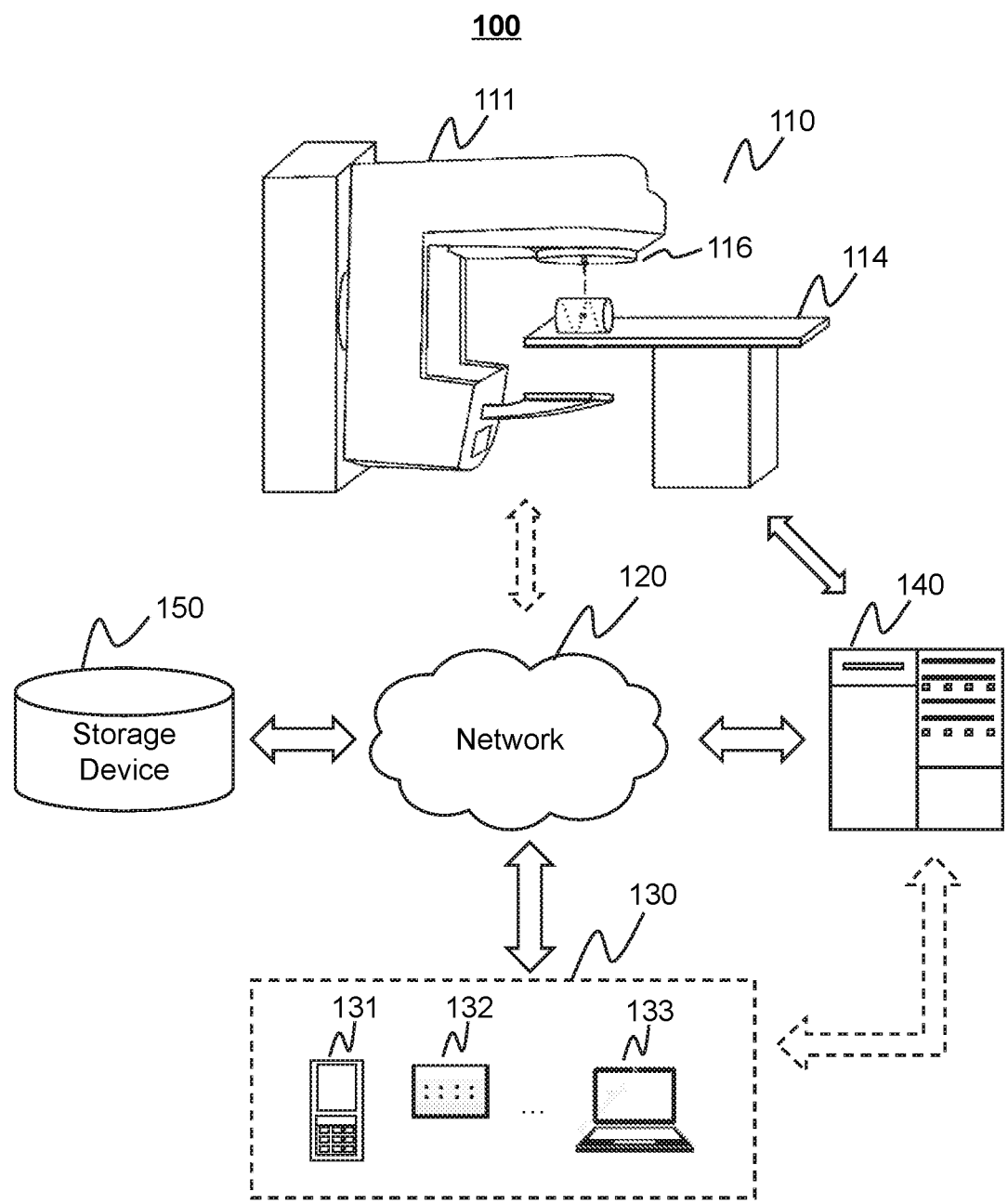
FIG. 1 is a schematic diagram illustrating an exemplary radiation system according to some embodiments of the present disclosure.

FIG. 1 is a schematic diagram illustrating an exemplary radiation system according to some embodiments of the present disclosure. As shown in FIG. 1, the radiation system 100 may include a treatment device 110, a network 120, one or more terminals 130, a processing device 140, and a storage device 150. The components in the radiation system 100 may be connected in one or more of various ways. Merely by way of example, the treatment device 110 may be connected to the processing device 140 through the network 120. As another example, the treatment device 110 may be connected to the processing device 140 directly as indicated by the bi-directional arrow in dotted lines linking the treatment device 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

In some embodiments, the treatment device 110 may be a radiotherapy (RT) device. In some embodiments, the RT device may deliver a radiation beam to an object (e.g., a patient, or a phantom) or a portion thereof. In some embodiments, the RT device may include a linear accelerator (also referred to as "linac"). The linac may generate and emit a radiation beam (e.g., an X-ray beam) from a treatment head 116. The radiation beam may pass through one or more collimators (e.g., a multi-leaf collimator (MLC)) of certain shapes, and enter into the object. In some embodiments, the radiation beam may include electrons, photons, or other types of radiation. In some embodiments, the energy of the radiation beam may be in the megavoltage range (e.g., >1 MeV), and may therefore be referred to as a megavoltage beam. The treatment head 116 may be coupled to a gantry 111. The gantry 111 may rotate, for example, clockwise or counter-clockwise around a gantry rotation axis. In some embodiments, the treatment head 116 may rotate along with the gantry 111. In some embodiments, the RT device may include a table 114 configured to support the object during a radiation treatment.

In some embodiments, the object may be biological or non-biological. Merely by way of example, the object may include a patient, an organ, a tissue, a specimen, a man-made object, a phantom, etc. In some embodiments, the object to be scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

In some embodiments, before or during a radiation treatment, an ionization chamber (not shown in FIG. 1) may be used to monitor or detect an intensity of radiation beams delivered by the treatment head 116. More descriptions of the ionization chamber may be found elsewhere in the present disclosure (e.g., FIGS. 4-13 and descriptions thereof).

The network 120 may include any suitable network that can facilitate the exchange of information and/or data for the radiation system 100. In some embodiments, one or more components of the radiation system 100 (e.g., the treatment device 110, the terminal 130, the processing device 140, the storage device 150, etc.) may communicate information and/or data with one or more other components of the radiation system 100 via the network 120. For example, the processing device 140 may send command(s) or instruction (s) to the treatment device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the treatment device 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the treatment device 110, the terminal 130, and/or the storage device 150 via the network 120. As another example, the processing device 140 may cause or control an equalization of a pressure of a radiation sensitive material in the ionization chamber and a pressure of the ambient air outside the ionization chamber. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140, or a portion of the processing device 140 may be integrated into the treatment device 110.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, removable storage, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiation system 100 (e.g., the processing device 140, the terminal 130, etc.). One or more components of the radiation system 100 may access the data or instructions stored in the storage device 150 via the network 120. In some embodiments, the storage device 150 may be directly connected to or communicate with one or more other components of the radiation system 100 (e.g., the processing device 140, the terminal 130, etc.). In some embodiments, the storage device 150 may be part of the processing device 140.

FIG. 2 is a schematic diagram illustrating exemplary hardware and software components of a computing device according to some embodiments of the present disclosure. The computing device 200 may be a general purpose computer or a special purpose computer; both may be used to implement a radiation system 100 of the present disclosure. In some embodiments, the processing device 140 may be implemented on the computing device 200, via its hardware, software program, firmware, or a combination thereof. Although only one such computer is shown, for convenience, the computer functions as described herein may be implemented in a distributed manner on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processor in accordance with techniques described herein. The computer instructions may include, for example, routines, programs, objects, components, data structures, procedures, modules, and functions, which perform particular functions described herein. For example, the processor 210 may detect a first pressure of a radiation sensitive material inside an ionization chamber. In some embodiments, the processor 210 may detect a second pressure of the ambient air outside the ionization chamber. In some embodiments, the processor 210 may equalize the first pressure and the second pressure by allowing the radiation sensitive material to flow between a reservoir of the radiation sensitive material and the ionization chamber. For instance, the flow of the radiation sensitive material between a reservoir and the ionization chamber may be facilitated using a pump.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the treatment device 110, the terminal 130, the storage device 150, and/or any other component of the radiation system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for equalizing the pressure of the radiation sensitive material in the ionization chamber.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the treatment device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
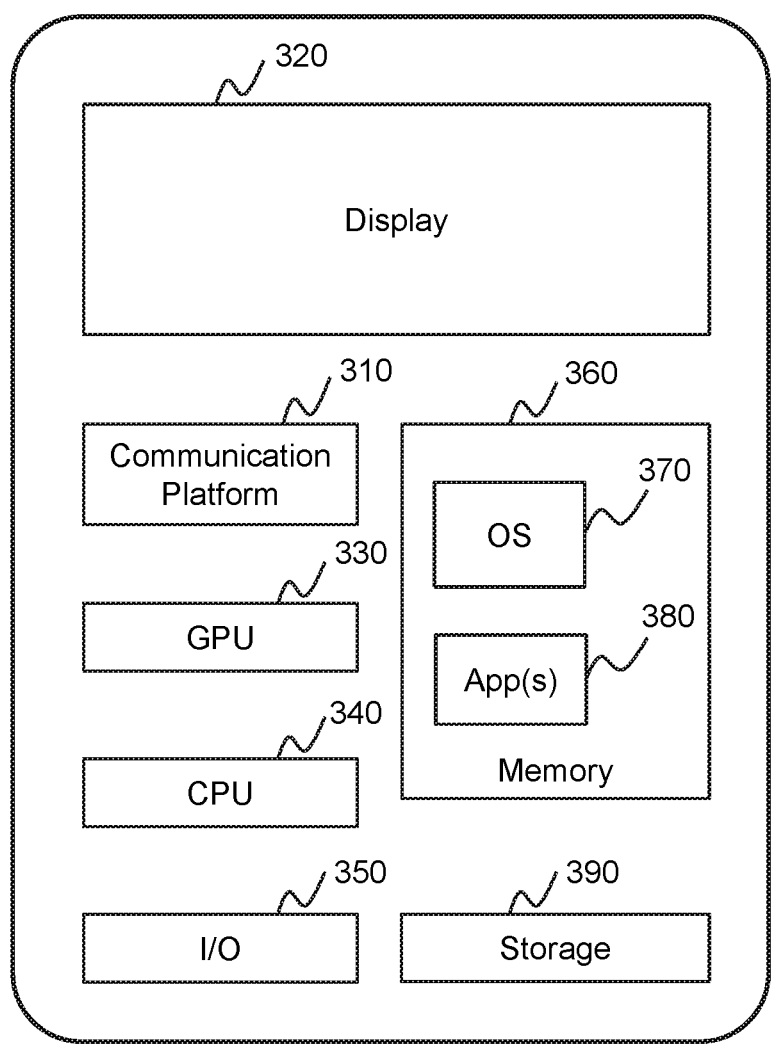
FIG. 3 is a schematic diagram illustrating exemplary hardware and/or software components of an exemplary mobile device that is configured to implement a specific system disclosed in the present disclosure.

FIG. 3 is a schematic diagram illustrating exemplary hardware and/or software components of an exemplary mobile device that is configured to implement a specific system disclosed in the present disclosure. As illustrated in FIG. 3, the mobile device 300 may include a communication unit 310, a display 320, a graphics processing unit (GPU) 330, a CPU 340, an I/O 350, a storage 390, and a memory 360. In some embodiments, any other suitable component, including but not limited to a system bus or a controller (not shown), may also be included in the mobile device 300. In some embodiments, a mobile operating system 370 (e.g., IOS™, Android™, Windows Phone™, Harmony OS, etc.) and one or more applications 380 may be loaded into the memory 360 from the storage 390 in order to be executed by the CPU 340. The applications 380 may include a browser or any other suitable mobile apps for receiving and rendering information relating to pressure equalization or other information from the processing device 140. User interactions with the information stream may be achieved via the I/O 350 and provided to the processing device 140 and/or other components of the radiation system 100 via the network 120. In some embodiments, a user may input parameters to the radiation system 100, via the mobile device 300.

In order to implement various modules, units and their functions described above, a computer hardware platform may be used as hardware platforms of one or more elements (e.g., the processing device 140 and/or other components of the radiation system 100 described in FIG. 1). Since these hardware elements, operating systems and program languages are common; it may be assumed that persons skilled in the art may be familiar with these techniques and they may be able to provide information needed in the pressure equalization according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
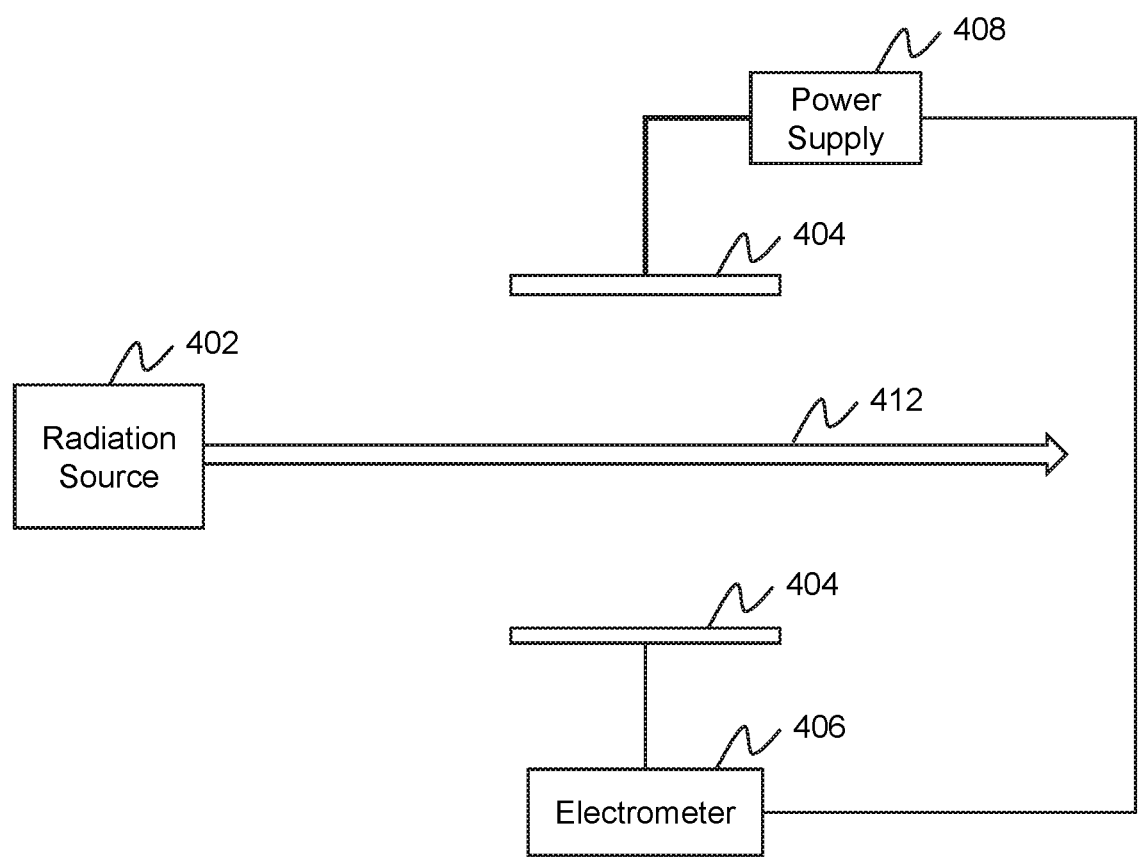
FIG. 4 is a schematic diagram illustrating an exemplary ionization chamber according to some embodiments of the present disclosure.

FIG. 4 is a schematic diagram illustrating an exemplary ionization chamber according to some embodiments of the present disclosure. The ionization chamber may be used as a radiation dosimetry configured to detect and/or measure radiation dose(s) of radiation beams. In some embodiments, the ionization chamber may detect and/or measure radiation dose(s) based on an ionization current generated by direct ionization of a radiation sensitive material through the application of an electric field. As shown in FIG. 4, the ionization chamber 400 may include one or more electrodes 404, an electrometer 406. In some embodiments, a power supply 408 may provide power for the ionization chamber 400. The ionization chamber 400 may be configured to detect the radiation dose of a radiation beam 412 generated from a radiation source 402. In some embodiments, the radiation beam 412 may be delivered from the radiation source 402 to the ionization chamber 400. It should be noted that the radiation source 402 and the radiation beam 412 are shown in FIG. 4 for illustration purposes, and not intended to limit the scope of the present disclosure. For example, the radiation beam 412 may be of any suitable type, for example, a fan beam, a cone beam, a parallel beam, etc. As another example, an incidence direction of the radiation beam 412 relative to the ionization chamber 400 (e.g., an incident angle of the radiation beam 412 relative to a wall of the ionization chamber 400) may have various angles (e.g., 10°, 20°, 30°, 40°, 50°, 60°, 90°, 120°, 150°, etc.). The incidence direction (e.g., the solid arrow in FIG. 4) of the radiation beam 412 perpendicular to the ionization chamber 400 in FIG. 4 is merely provided for the purposes of illustration, and not intended to limit the scope of the present disclosure. In some embodiments, one or more parameters (such as an intensity, a radiation time, an incidence direction, and so on) of the radiation beam 412 may be set according to a radiation treatment plan.

In some embodiments, the radiation source 402 may generate and/or emit one or more radiation beams. Exemplary radiation beams may include an X-ray beam, a γ-ray beam, an α-ray beam, a β-ray beam, a neutron beam, or the like, or a combination thereof. In some embodiments, the radiation source 402 may be a portion of a radiation device, for example, a radiotherapy device, a positron emission tomography (PET) device (in which a scanned object (e.g., a patient) may be regarded as a radiation source), a single-photon emission computed tomography (SPECT) device, a computed tomography (CT) device, or a multi-modality device (e.g., a PET-MRI device, a SPECT-MRI device, a PET-CT device, etc.).

In some embodiments, one or more of the electrode(s) 404 may be configured to generate an electric field in the ionization chamber 400. In some embodiments, the electrode(s) 404 may include at least one anode and at least one cathode. The at least one anode and the at least one cathode may be operably coupled to (e.g., connected with) the power supply 408. In some embodiments, the electrode(s) 404 may include graphite electrode(s), semi-metal electrode(s) (such as silicon electrode(s)), metal electrode(s) (such as platinum electrode(s), copper electrode(s), lead electrode(s), gold electrode(s), silver electrode(s)), or the like. In some embodiments, the electrode(s) 404 may be arranged in the form of parallel plates, and the ionization chamber 400 may be regarded as a parallel-plate ionization chamber. In some embodiments, the electrode(s) 404 may be arranged in the form of cylindrical electrode(s) (e.g., a cylindrical electrode arranged with a coaxially located internal opposite electrode, or two coaxial cylindrical electrodes, or the like), and the ionization chamber 400 may be regarded as a cylindrical ionization chamber. In some embodiments, the electrode(s) 404 may be arranged in the form of spherical electrode(s) (e.g., a spherical electrode arranged with a coaxially located internal opposite electrode, or two concentric spherical electrodes, or the like), and the ionization chamber 400 may be regarded as a spherical ionization chamber.

In some embodiments, the ionization chamber 400 may be filled with a radiation sensitive material. In some embodiments, the electrode(s) 404 may be immersed in the radiation sensitive material. In some embodiments, the radiation sensitive material may be configured to generate a plurality of ion-pairs. In some embodiments, the radiation sensitive material in the ionization chamber 400 may be a fluid material such as a gas or a liquid. In some embodiments, the gas may include the air (e.g., the atmospheric air), a noble gas (e.g., argon, xenon), or the like, or any combination thereof. In some embodiments, the liquid may include water, oil, etc. In general, the material with which the ionization chamber is filled may include any ionizable material. If a radiation beam passes through the ionization chamber 400, the radiation sensitive material filling the ionization chamber 400 may be ionized by the electric field generated by the electrode(s) 404, and a plurality of ion-pairs may be generated. The plurality of ion-pairs may include positive ions and dissociated electrons. In some embodiments, one ion-pair may include one positive ion and one dissociated electron. The positive ions and dissociated electrons may move to the electrodes (e.g., two electrodes) of opposite polarities, respectively, under the influence of the electric field, and accordingly, an ionization current may be generated. In some embodiments, the plurality of ion-pairs may be proportional to the number (or count) of ions and/or electrons generated by the ionization of the radiation sensitive material. The ionization of the radiation sensitive material may correlate with the radiation dose of the radiation beam(s). The generated ion-pairs may produce the ionization current. Accordingly, the ionization current may be proportional to the radiation dose. Therefore, the radiation dose may be detected or measured by detecting the ionization current.

In some embodiments, the electrometer 406 may be configured to detect or measure the ionization current conducted by one or more of the electrode(s) 404. In some embodiments, the electrometer 406 may include a gold-leaf electrometer, an early quadrant electrometer, a Coulomb's electrometer, a Peltier electrometer, a vibrating reed electrometer, a valve electrometer, a solid-state electrometer, or the like.

In some embodiments, the power supply 408 may be configured to provide a voltage potential for one or more of the electrode(s) 404 to generate the electric field. In some embodiments, the voltage potential may be sufficiently large to enable the ionization chamber 400 to work continuously by mopping up the plurality of ion-pairs, preventing the recombination of the plurality of ion-pairs which may diminish the ionization current. The power supply 408 may include a direct current (DC) power supply, a programmable power supply, an uninterruptible power supply, or the like. In some embodiments, the power supply 408 may be configured to provide a voltage potential of an adjustable magnitude.

In some embodiments, the ionization chamber 400 may be used to detect the radiation dose of the radiation beam(s) 412 delivered from the radiation source 402 when the radiation source 402 is working. For example, the ionization chamber 400 may be used to detect the radiation dose before a radiation therapy process or imaging process to make sure the radiation beam(s) of a desired radiation dose be emitted. As another example, the ionization chamber 400 may be used to detect the radiation dose during the radiation therapy process or imaging process to verify that radiation beam(s) with a planned radiation dose are delivered to an object to be treated or imaged. In some embodiments, the ionization chamber 400 may be used to detect the radiation dose when no object is present (e.g., before a radiation therapy process or imaging process). In some embodiments, the ionization chamber 400 may be placed above an object (not shown) (e.g., a patient to be treated or imaged). The object may be biological or non-biological to be irradiated. More descriptions of the object may be found elsewhere in the present disclosure (e.g., FIG. 1 and descriptions thereof). It should be noted that the ionization chamber 400 does not significantly absorb or attenuate the radiation beam traversing the ionization chamber 400, and thus, the intensity of the radiation beam traversing the ionization chamber 400 may be substantially equal to the intensity of the radiation beam entering the ionization chamber 400.

Figure 5:
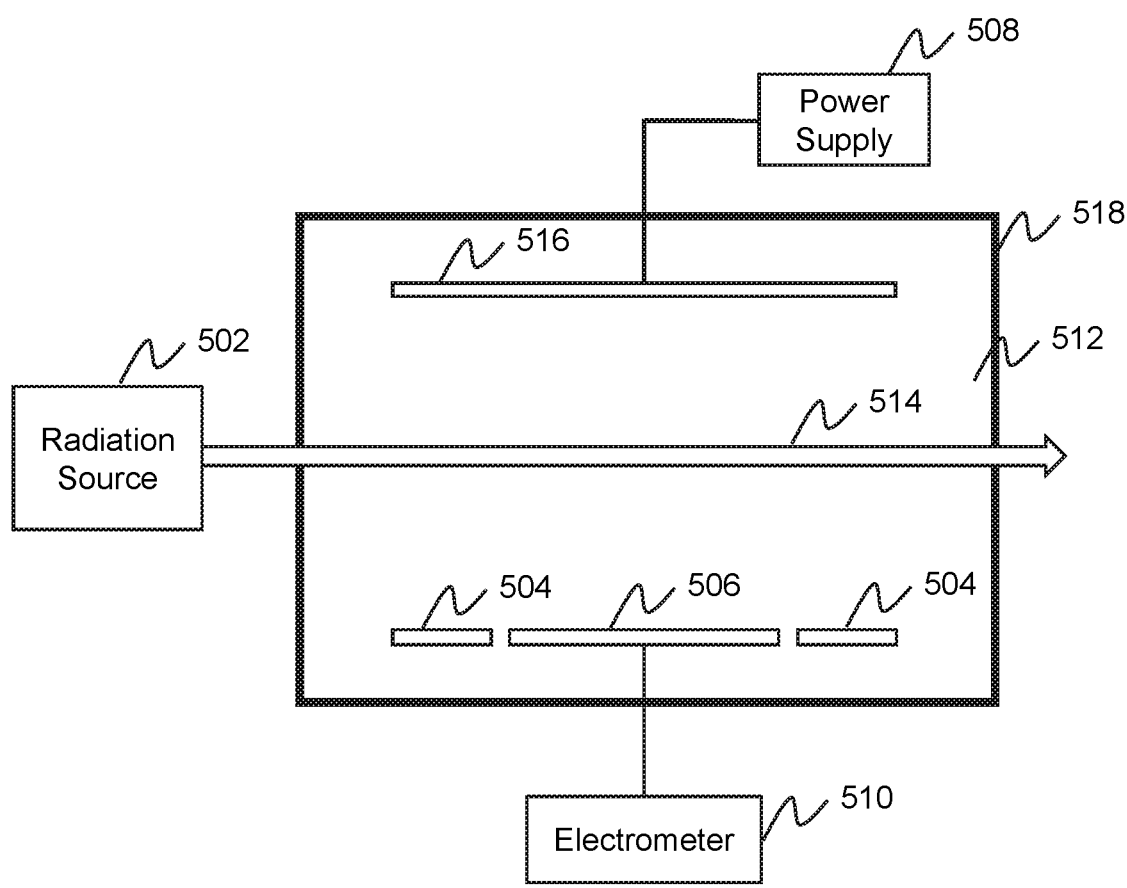
FIG. 5 is a schematic diagram illustrating an exemplary parallel-plate ionization chamber according to some embodiments of the present disclosure.

FIG. 5 is a schematic diagram illustrating an exemplary parallel-plate ionization chamber according to some embodiments of the present disclosure. As shown in FIG. 5, the parallel-plate ionization chamber 500 may include one or more guard ring electrodes 504, a measuring (or collecting) electrode 506, a power supply 508, an electrometer 510, a cavity 512 (or a chamber volume), and a polarizing (or biasing) electrode 516. The ionization chamber 500 may be configured to detect the radiation dose of a radiation beam 514 generated from a radiation source 502. It should be noted that the radiation source 502 and the radiation beam 514 are shown in FIG. 5 for illustration purposes, and not intended to limit the scope of the present disclosure. In some embodiments, one or more parameters (such as an intensity, a radiation time, an incidence direction, and so on) of the radiation beam 514 may be set according to a radiation treatment plan.

In some embodiments, the radiation source 502 may generate and/or emit one or more radiation beams. The radiation source 502 and the radiation beam 514 may be the same as or similar to the radiation source 402 and the radiation beam 412, and more descriptions of the radiation source and the radiation beam may be found elsewhere in the present disclosure (e.g., FIG. 4 and descriptions thereof).

In some embodiments, the polarizing (or biasing) electrode 516 may be configured to generate an electric field in the chamber volume. In some embodiments, the polarizing (or biasing) electrode 516 may be operably coupled to (e.g., connected with) a positive pole or negative pole of the power supply 508, and the power supply 508 may provide a voltage potential for the polarizing (or biasing) electrode 516 and cause the polarizing (or biasing) electrode 516 to generate the electric field. In some embodiments, the measuring (or collecting) electrode 506 may be configured to collect a plurality of ion-pairs generated in the electric field (or measure a charge or current that is associated with the radiation sensitive material and produced, based on the electric field, in the chamber volume). In some embodiments, the measuring (or collecting) electrode 506 may be operably coupled to (e.g., connected with) the electrometer 510. In some embodiments, the guard ring electrode(s) 504 may be configured to eliminate or compensate distortion (or "edge effect") of the electric field around the edges of the measuring electrode 506 and/or minimize leakage currents. In some embodiments, one or more of the guard ring electrode(s) 504 may be earthed or grounded (not shown). In some embodiments, the guard ring electrode(s) 504, the measuring (or collecting) electrode 506, and/or the polarizing (or biasing) electrode 516 may include graphite electrodes, metal electrodes (such as platinum electrode(s), copper electrode(s), lead electrode(s), gold electrode(s), silver electrode(s)), or the like. In some embodiments, the guard ring electrode(s) 504, the measuring (or collecting) electrode 506, and/or the polarizing (or biasing) electrode 516 may be made of a same electrode material or different electrode materials. More descriptions of the electrode(s) may be found elsewhere in the present disclosure (e.g., FIG. 4 and descriptions thereof).

In some embodiments, the power supply 508 may be configured to provide a voltage potential for the parallel-plate ionization chamber 500 (e.g., the polarizing (or biasing) electrode 516) to generate the electric field. More descriptions of the power supply may be found elsewhere in the present disclosure (e.g., FIG. 4 and descriptions thereof).

In some embodiments, the electrometer 510 may be configured to detect or measure the ionization current collected by the measuring (or collecting) electrode 506. More descriptions of the electrometer may be found elsewhere in the present disclosure (e.g., FIG. 4 and descriptions thereof).

In some embodiments, the cavity 512 (or chamber volume) may be configured to provide a measuring space to accommodate the guard ring electrode(s) 504, the measuring (or collecting) electrode 506, the polarizing (or biasing) electrode 516, and/or a radiation sensitive material. In some embodiments, the cavity 512 may be defined or formed by a chamber housing 518 of the parallel-plate ionization chamber 500. The chamber housing 518 may be of any suitable shape (e.g., a cuboid shape, a cubic shape, a cylindrical shape, or the like). The chamber housing 518 may include one or more chamber walls. In some embodiments, the one or more chamber walls may be made of a high atomic number material (e.g., tungsten, lead). In some embodiments, the chamber housing 518 may be sealed. In some embodiments, the chamber housing 518 may be unsealed. In some embodiments, the cavity 512 (or chamber volume) may be at least partially filled with the radiation sensitive material. In some embodiments, the radiation sensitive material may be a fluid material such as a gas or a liquid. In some embodiments, the gas may include ambient air, a noble gas (e.g., argon, xenon), or the like, or any combination thereof. In some embodiments, the liquid may include water, oil, etc.

It should be noted that in some embodiments, the ionization chamber 400 or the parallel-plate ionization chamber 500 may be a hybrid of a sealed compartment and an unsealed compartment. In some embodiments, the hybrid ionization chamber of a sealed compartment and an unsealed compartment may include a chamber housing including one or more chamber walls, a chamber volume inside the chamber housing, and/or a pressure adjustment apparatus operably coupled to at least one wall of the one or more chamber walls. In some embodiments, the at least one wall may have a thickness between 10 micrometers and 2 millimeters, for example, 20 micrometers, 30 micrometers, 40 micrometers, 50 micrometers, 75 micrometers, 100 micrometers, 150 micrometers, 200 micrometers, 300 micrometers, 400 micrometers, 500 micrometers, 750 micrometers, 1000 micrometers, 1200 micrometers, 1500 micrometers, 1750 micrometers, etc. In some embodiments, the chamber volume may be filled with a radiation sensitive material. In some embodiments, the pressure adjustment apparatus may be configured to equalize a first pressure of the radiation sensitive material inside the chamber volume and a second pressure of the ambient air outside the chamber housing. In some embodiments, the chamber volume may be airtight. In some embodiments, the at least one wall may include a hole so that the chamber volume is in fluid communication with the pressure adjustment apparatus. In some embodiments, the pressure adjustment apparatus may prevent the chamber volume from fluid communication with the ambient air. In some embodiments, the hybrid ionization chamber of a sealed compartment and an unsealed compartment may include one or more electrodes that are configured to establish an electric field in the chamber volume and measure a charge or current that is associated with the radiation sensitive material and produced, based on the electric field, in the chamber volume. Descriptions of exemplary pressure adjustment apparatuses may be found elsewhere in the present disclosure (e.g., FIGS. 6-13 and descriptions thereof).

Figure 6A:
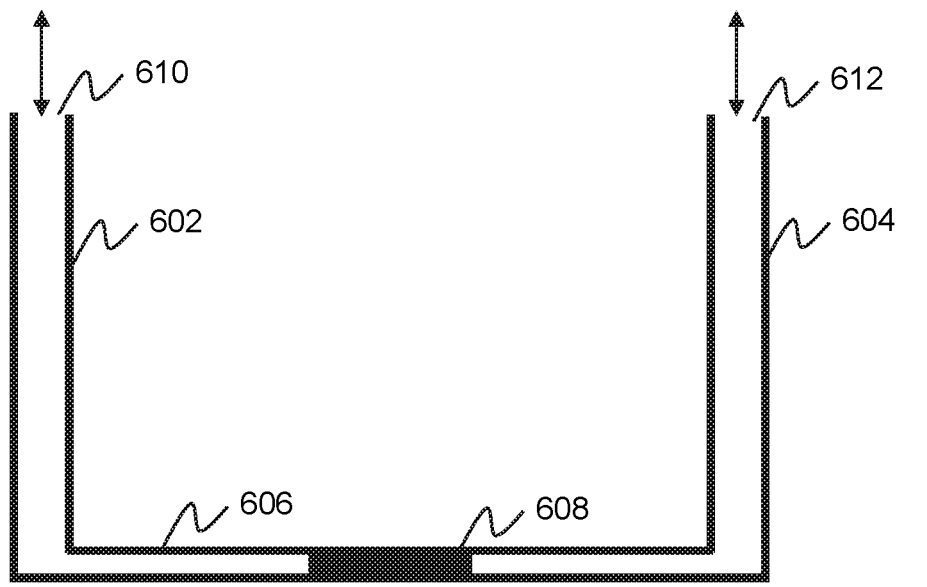
FIGS. 6A and 6B are schematic diagrams illustrating an exemplary pressure adjustment apparatus according to some embodiments of the present disclosure.
Figure 6B:
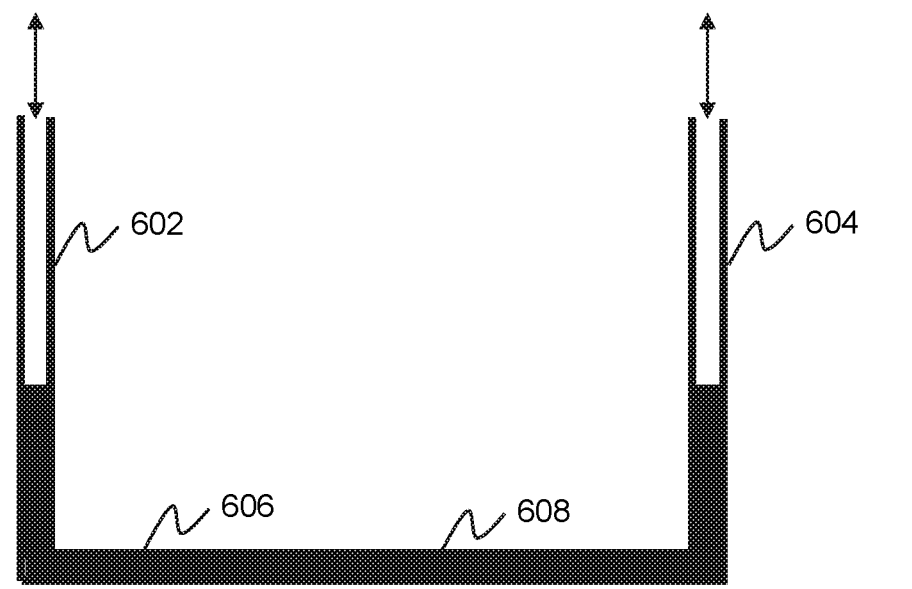

FIGS. 6A and 6B are schematic diagrams illustrating an exemplary pressure adjustment apparatus according to some embodiments of the present disclosure. In some embodiments, the pressure adjustment apparatus 600a (or 600b) may include one or more tubes configured to form a fluid flow passage, and a fluid material 608. The fluid material 608 may be trapped inside the tube(s) (or the fluid flow passage). In some embodiments, the fluid material 608 may move (within the tube(s)) to equalize a first pressure of the radiation sensitive material inside the chamber volume and a second pressure of the ambient air outside the chamber housing.

In some embodiments, as shown in FIGS. 6A and 6B, the pressure adjustment apparatus 600a (or 600b) may include only one tube. The tube may form the fluid flow passage to allow a fluid (e.g., a gas, and/or a liquid) to flow to equalize the first pressure and the second pressure. The tube may include a first end 610 and a second end 612. The first end 610 may be open to a chamber volume of an ionization chamber (e.g., the ionization chamber 400, the parallel-plate ionization chamber 500) through at least one wall of the ionization chamber. In some embodiments, a space 613 between the first end 610 of the tube and the fluid material 608 may be at least partially filled with the radiation sensitive material, and the space may be in fluid communication with the chamber volume. The second end 612 may be open to the ambient air (also referred to as the atmosphere air). The volume of the space may change when the fluid material moves within the fluid flow passage, thereby achieving pressure adjustment. In some embodiments, the tube may include one or more portions, for example, a first portion (see 602), a second portion (see 604), and a third portion (see 606), or the like. Different portions of the tube may have the same or different dimensions (e.g., diameters, lengths, widths, wall thicknesses, etc.). Different portions of the tube may be made of the same or different materials (e.g., plastic, glass, ceramics, rubber, silicon dioxide, silica gel, flexible quartz, metals (e.g., copper, lead, iron, steel, silver, gold, chromium, rare-earth metal, etc.), or the like, or an alloy thereof, or any combination thereof). In some embodiments, one or more portions of the tube may be flexible. In some embodiments, one or more portions of the tube may be rigid.

Alternatively, as shown in FIGS. 6A and 6B, the pressure adjustment apparatus 600a (or 600b) may include two or more tubes, for example, a first tube (see 602), a second tube (see 604), and/or a third tube (see 606). The first tube, the second tube, and/or the third tube may be connected to form the fluid flow passage to allow a fluid (e.g., a gas, and/or a liquid) to flow to equalize the first pressure and the second pressure. It should be noted that the pressure adjustment apparatus 600a (or 600b) may either include only one tube with one or more portions, or include one or more tubes connected to from the fluid flow passage, the following descriptions are merely provided for the purposes of illustration, and not intended to limit the scope of the present disclosure. For brevity, 602 may indicate a first portion of the fluid flow passage (which may be a first portion of a tube or a first tube), 604 may indicate a second portion of the fluid flow passage (which may be a second portion of a tube or a second tube), and 606 may indicate a third portion of the fluid flow passage (which may be a third portion of a tube or a third tube).

In some embodiments, the first portion of the fluid flow passage 602 may be operably coupled to (e.g., connected to) an ionization chamber and the third portion of the fluid flow passage 606. In some embodiments, the first portion of the fluid flow passage 602 may be made of a material including, for example, a non-metallic material (e.g., plastic, glass, ceramics, rubber, silicon dioxide, silica gel, flexible quartz, or the like), a metallic material (e.g., copper, lead, iron, steel, silver, gold, chromium, rare-earth metal, or the like), an alloy, or any combination thereof. In some embodiments, the first portion of the fluid flow passage 602 may have a uniform size and/or shape along an axis of the first portion of the fluid flow passage 602. For example, the first portion of the fluid flow passage 602 may be cylindrical of a diameter (e.g., 1 millimeter). In some embodiments, the first portion of the fluid flow passage 602 may have a varying size and/or shape along the axis of the first portion of the fluid flow passage 602. For example, the first portion of the fluid flow passage 602 may have a substantially conical shape. As another example, a cross section of one end of the first portion of the fluid flow passage 602 may have a circular shape (e.g., with a diameter of 1 millimeter), while a cross section of another end of the first portion of the fluid flow passage 602 may have a hexagon shape (e.g., each side of which is 0.5 millimeters long). In some embodiments, the first portion of the fluid flow passage 602 may be at least partially filled with the radiation sensitive material which is the same as that in the ionization chamber. In some embodiments, a first part of the first portion of the fluid flow passage 602 close (or next) to the ionization chamber may be at least partially filled with the radiation sensitive material which is the same as that in the ionization chamber, and a second part of the first portion of the fluid flow passage 602 close (or next) to the third portion of the fluid flow passage 606 may be filled with the fluid material 608 which is the same as that in the third portion of the fluid flow passage 606. In some embodiments, at least one wall of the ionization chamber may include a hole, and the first end 610 of the first portion of the fluid flow passage 602 may be operably coupled to (e.g., airtightly connected to) the at least one wall except for the hole. In some embodiments, the radiation sensitive material inside the ionization chamber may be isolated from the ambient air because of the fluid material 608. In some embodiments, the first end 610 may be directly connected to the at least one wall. In some embodiments, the first end 610 may be connected to the at least one wall through a connecting piece such as a flange, a reversible cock, a reversible valve, or the like.

In some embodiments, the third portion of the fluid flow passage 606 may be operably coupled to (e.g., connected to) the first portion of the fluid flow passage 602 and the second portion of the fluid flow passage 604. In some embodiments, the material, the size, and/or the shape of the third portion of the fluid flow passage 606 may be the same as or different from those of the first portion of the fluid flow passage 602 and/or the second portion of the fluid flow passage 604. Merely by way of example, the third portion of the fluid flow passage 606 may be a capillary, while either one of the first portion of the fluid flow passage 602 or the second portion of the fluid flow passage 604 may be of a dimension larger than that of the third portion of the fluid flow passage 606. As another example, the first portion of the fluid flow passage 602 and/or the second portion of the fluid flow passage 604 may each include a plastic tube or a stainless steel tube. In some embodiments, the third portion of the fluid flow passage 606 may be of a fixed length. In some embodiments, the third portion of the fluid flow passage 606 may be at least partially filled with the fluid material 608. For instance, a first part of the third portion of the fluid flow passage 606 close (or next) to the first portion of the fluid flow passage 602 may be at least partially filled with the radiation sensitive material which is the same as that in the ionization chamber, a second part of the third portion of the fluid flow passage 606 close (or next) to the second portion of the fluid flow passage 604 may be filled with the ambient air, while the remaining part of the third portion of the fluid flow passage 606 may be filled with the fluid material 608.

In some embodiments, the second portion of the fluid flow passage 604 may be operably coupled to (e.g., connected to) the third portion of the fluid flow passage 606. In some embodiments, the second end 612 of the second portion of the fluid flow passage 604 may be open to the ambient air (also referred to as the atmosphere). In some embodiments, the material, the size, and the shape of the second portion of the fluid flow passage 604 may be the same as or different from those of the first portion of the fluid flow passage 602 and/or the third portion of the fluid flow passage 606. In some embodiments, the second portion of the fluid flow passage 604 may be at least partially filled with the ambient air. In some embodiments, a first part of the second portion of the fluid flow passage 604 close (or next) to the second end 612 may be filled with the ambient air, while a second part of the second portion of the fluid flow passage 604 close (or next) to the third portion of the fluid flow passage 606 may be filled with the fluid material 608 which is the same as that in the third portion of the fluid flow passage 606.

In some embodiments, the first portion of the fluid flow passage 602, the second portion of the fluid flow passage 604, and the third portion of the fluid flow passage 606 may be configured as an integral piece (e.g., an integral tube). In some embodiments, the first portion of the fluid flow passage 602, the second portion of the fluid flow passage 604, and the third portion of the fluid flow passage 606 may be connected airtightly. In some embodiments, the first portion of the fluid flow passage 602, the second portion of the fluid flow passage 604, and the third portion of the fluid flow passage 606 may be connected through, for example, a threaded connection, a flange connection, a welded connection, a bell-and-spigot connection, a bonding connection, a fusion connection, or the like, or any combination thereof. For example, if the third portion of the fluid flow passage 606 is a capillary, and the first portion of the fluid flow passage 602 and the third portion of the fluid flow passage 606 are plastic tubes, the plastic tubes may be airtightly sheathed on the capillary. In some embodiments, the first portion of the fluid flow passage 602 and the second portion of the fluid flow passage 604 may be omitted, and the third portion of the fluid flow passage 606 may be operably coupled to (e.g., connected to) the ionization chamber directly.

In some embodiments, the fluid material 608 may be configured to form an airtight plug or seal (within the tube(s)) that isolates the radiation sensitive material (inside the ionization chamber, and/or the first portion of the fluid flow passage 602) from the ambient air. In some embodiments, the fluid material 608 may be further configured to form an airtight plug or seal (within the tube(s)) that prevents the ambient air from affecting the humidity and/or the temperature of the radiation sensitive material or the chamber volume. In some embodiments, the viscosity of the fluid material 608 may be in a range so that the fluid material 608 can move driven by a pressure difference (between the first pressure and the second pressure) of a magnitude of interest (e.g., 10 millibars, 50 millibars, 100 millibars). In some embodiments, the surface tension of the fluid material 608 may need to be high enough such that the pressure difference (between the first pressure and the second pressure) does not break the airtight plug or seal provided by the fluid material 608. In some embodiments, the fluid material 608 may be hydrophobic. In some embodiments, the fluid material 608 may include a nonpolar solvent such as an oil, an alkane, an olefin, or the like, or any combination thereof. In some embodiments, the material of the third portion of the fluid flow passage 606 may be selected based on the property (such as the viscosity, the surface tension, or the like) of the fluid material 608. For example, if the viscosity of the fluid material 608 is relatively large and the surface tension of the fluid material 608 is relatively high, the third portion of the fluid flow passage 606 may be made of a material providing a relatively smooth inner wall, such as metal, glass, or the like. As another example, if the viscosity of the fluid material 608 is relatively small and the surface tension of the fluid material 608 is relatively low, the third portion of the fluid flow passage 606 may be made of a material providing a relatively rugged inner wall, such as ceramics, rubber, silicon dioxide, silica gel, flexible quartz, or the like.

In some embodiments, the third portion of the fluid flow passage 606 may be arranged horizontally. In some embodiments, the third portion of the fluid flow passage 606 may be shaped into, for example, a spiral or helix, in order to increase a volume and/or a travel length of the fluid material 608 without increasing the overall length of the pressure adjustment apparatus. In some embodiments, the first portion of the fluid flow passage 602 and/or the second portion of the fluid flow passage 604 may be arranged horizontality, perpendicularity, or at a certain angle (e.g., 10°, 20°, 30°, 40°, 50°, 60°, 100°, 120°, 150°, etc.) with the horizontality. In some embodiments, the first portion of the fluid flow passage 602 and/or the second portion of the fluid flow passage 604 may have a curved shape. In some embodiments, the first portion of the fluid flow passage 602 and/or the second portion of the fluid flow passage 604 may be flexible.

In some embodiments, if the first pressure is equal to the second pressure, the fluid material 608 may remain stationary. For example, under an initial pressure equalization status of the pressure adjustment apparatus 600a (or 600b) as shown in FIGS. 6A and 6B, the first pressure may be equal to the second pressure, and the fluid material 608 may be stationary in the third portion of the fluid flow passage 606. In some embodiments, if the first pressure is different from the second pressure, the pressure difference between the first pressure and the second pressure may force the fluid material 608 to move until the first pressure and the second pressure are equalized. The movement of the fluid material 608 may cause a change in the volume of the radiation sensitive material, and accordingly, the first pressure can be adjusted. More descriptions of the pressure equalization may be found elsewhere in the present disclosure (e.g., FIGS. 7A and 7B and descriptions thereof). In some embodiments, the ionization chamber may have one or more holes in the walls of the chamber housing, and each of the one or more holes may be operably coupled to (e.g., connected to) a pressure adjustment apparatus (e.g., the pressure adjustment apparatus 600a (or 600b) illustrated in FIGS. 6A and 6B, the pressure adjustment apparatus 800 illustrated in FIG. 8, the pressure adjustment apparatus 1000 illustrated in FIG. 10, the pressure adjustment apparatus 1200 illustrated in FIG. 12, the pressure adjustment apparatus 1300 illustrated in FIG. 13). The pressure equalization may be realized by one or more of the pressure adjustment apparatuses operably coupled to (e.g., airtightly connected to) the ionization chamber. In some embodiments, the one or more pressure adjustment apparatuses may have a total volume that is larger than the volume of the fluid material 608, thereby preventing the fluid material 608 from exiting the pressure adjustment apparatus, e.g., flowing into the ionization chamber or exiting to the ambient air.

It should be noted that the above description of the pressure adjustment apparatus is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, at least a portion of the tube (e.g., the third portion of the fluid flow passage 606) may be or include a capillary, and the fluid material 608 may be trapped in the capillary. In some embodiments, the pressure adjustment apparatus 600a (or 600b) may further include a fourth portion of the fluid flow passage, a fifth portion of the fluid flow passage, etc., that are similar or parallel to the third portion of the fluid flow passage 606 to share the pressure difference between the first pressure and the second pressure and prevent the fluid material 608 from flowing into the ionization chamber or the ambient air. For example, the pressure adjustment apparatus 600*a* (or 600*b*) may include two or more capillaries in parallel, and the fluid material may be trapped in each of the two or more capillaries. In some embodiments, the first portion of the fluid flow passage 602 and/or the second portion of the fluid flow passage 604 may have a larger diameter than the third portion of the fluid flow passage 606, or the first end 610 and/or the second end 612 may be coupled to larger tubes than the third portion of the fluid flow passage 606 that can capture the fluid material 608, so that the fluid material 608 may be prevented from flowing into the ionization chamber or the ambient air.

Figure 7A:
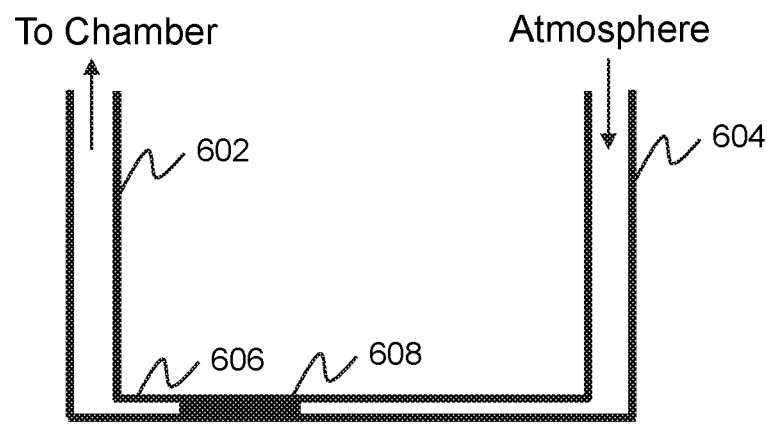
FIGS. 7A and 7B are schematic diagrams illustrating the pressure adjustment apparatus of FIGS. 6A and 6B under exemplary pressure equalization statuses according to some embodiments of the present disclosure.
Figure 7B:
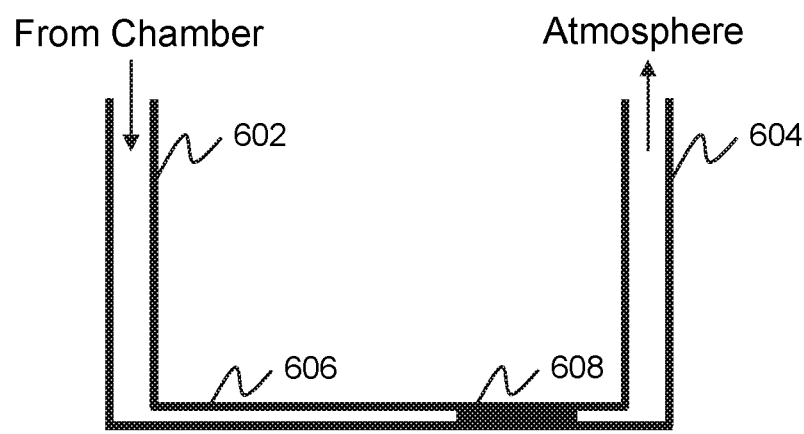

FIGS. 7A and 7B are schematic diagrams illustrating the pressure adjustment apparatus of FIGS. 6A and 6B under exemplary pressure equalization statuses according to some embodiments of the present disclosure.

In some embodiments, under an initial pressure equalization status of the pressure adjustment apparatus 600*a* (or 600*b*) as shown in FIGS. 6A and 6B, the first pressure is equal to the second pressure, and the fluid material 608 may remain stationary (e.g., the fluid material 608 may be stationary in the third portion of the fluid flow passage 606). If the first pressure is equal to the second pressure, the fluid material 608 may remain stationary. For example, the fluid material 608 may remain in the middle of the third portion of the fluid flow passage 606. In some embodiments, if the first pressure and/or the second pressure changes, the equilibrium state may break.

As shown in FIG. 7A, if the first pressure is lower than the second pressure (e.g., the first pressure decreases and/or the second pressure increases from the initial pressure equalization status or a previous pressure equalization status), the pressure difference between the second pressure and the first pressure may force the fluid material 608 to move towards the first portion of the fluid flow passage 602. Therefore, the ambient air may flow into the second portion of the fluid flow passage 604, the volume of the radiation sensitive material may reduce, and the first pressure may increase. In some embodiments, the fluid material 608 may be forced to move until the first pressure is equalized with the second pressure. If the first pressure and the second pressure are equalized again, the movement of the fluid material 608 may stop, and the fluid material 608 may reach a first pressure equalization status.

As shown in FIG. 7B, if the first pressure is larger than the second pressure (e.g., the first pressure increases and/or the second pressure decreases from the initial pressure equalization status or a previous pressure equalization status), the pressure difference between the first pressure and the second pressure may force the fluid material 608 to move towards the second portion of the fluid flow passage 604. Therefore, the ambient air may flow out from the second portion of the fluid flow passage 604, the volume of the radiation sensitive material may increase, and the first pressure may reduce. In some embodiments, the fluid material 608 may be forced to move until the first pressure is equalized with the second pressure. If the first pressure becomes equal to the second pressure again, the movement of the fluid material 608 may stop, and the fluid material 608 may reach a second pressure equalization status.

Figure 8:
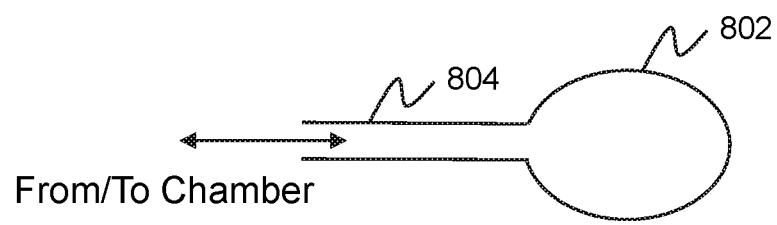
FIG. 8 is a schematic diagram illustrating another exemplary pressure adjustment apparatus according to some embodiments of the present disclosure.

FIG. 8 is a schematic diagram illustrating another exemplary pressure adjustment apparatus according to some embodiments of the present disclosure. As shown in FIG. 8, the pressure adjustment apparatus 800 may include an enclosure 802 and a tube 804.

In some embodiments, the enclosure 802 may be configured to adjust the pressure in the ionization chamber. In some embodiments, the enclosure 802 may function as a reservoir of the radiation sensitive material. In some embodiments, the enclosure 802 may be flexible. In some embodiments, the volume of the enclosure 802 may change (e.g., automatically) to equalize the first pressure of the radiation sensitive material inside the chamber volume and the second pressure of the ambient air outside the chamber housing. In some embodiments, the enclosure 802 may be implemented in the configuration of a balloon, a bellows, a flexible enclosure (e.g., a thin-walled enclosure), or the like. In some embodiments, the enclosure 802 may be of any suitable shape, such as a sphere, an ellipsoid, a column, a taper, or the like, or any combination thereof. In some embodiments, the enclosure 802 may be airtightly and operably connected to the tube 804. In some embodiments, the enclosure 802 may be nonpermeable for the radiation sensitive material and the ambient air.

In some embodiments, the tube 804 may include a first end and a second end. The first end may be open to the chamber volume, and the second end may be open to the enclosure 802. In some embodiments, the enclosure 802 may be in fluid communication with the chamber volume through the tube 804. In some embodiments, at least one wall of the chamber housing may include a hole, and the first end of the tube 804 may be airtightly connected to the at least one wall except for the hole. In some embodiments, the first end of the tube 804 may be directly connected to the at least one wall. In some embodiments, the first end of the tube 804 may be connected to the at least one wall through a connecting piece. In some embodiments, the enclosure 802 and the tube 804 may be airtight such that the radiation sensitive material inside the chamber volume, the enclosure 802, and the tube 804 may be isolated from the ambient air. In some embodiments, the tube 804 may be made of a material including for example, a non-metallic material (e.g., plastic, glass, ceramics, rubber, silicon dioxide, silica gel, flexible quartz, or the like), a metallic material (e.g., copper, lead, iron, steel, silver, gold, chromium, rare-earth metal, or the like), or an alloy thereof, or any combination thereof. In some embodiments, the tube 804 may have a uniform size and/or shape along an axis of the tube 804. For example, the tube 804 may be cylindrical of a diameter (e.g., 1 millimeter). In some embodiments, the tube 804 may have a varying size and/or shape along the axis of the tube 804. For example, the tube 804 may have a substantially conical shape. As another example, a cross section of one end of the tube 804 may have a circular shape (e.g., with a diameter of 1 millimeter), while a cross section of another end of the tube 804 may have a hexagon shape (e.g., each side of which is 0.5 millimeters long).

In some embodiments, the enclosure 802 may be made of a first material having a first elastic modulus, and the one or more chamber walls may be made of one or more second materials each having a second elastic modulus. The first elastic modulus may be lower than the second elastic modulus so that the volume of the enclosure 802 can change to equilibrate the first pressure and the second pressure. In some embodiments, if the first pressure is equal to the second pressure, the enclosure 802 may remain stationary. For example, the initial pressure equalization status of the pressure adjustment apparatus 800 may be shown in FIG. 8, in which the first pressure is equal to the second pressure, and the enclosure 802 is stationary. In some embodiments, if the first pressure becomes different from the second pressure, a pressure difference between the first pressure and the second pressure may force the enclosure 802 to distort. Accordingly, the volume of the enclosure 802 may change, and the first pressure can be adjusted. More descriptions of the pressure equalization may be found elsewhere in the present disclosure (e.g., FIGS. 9A and 9B and descriptions thereof).

Figure 9A:
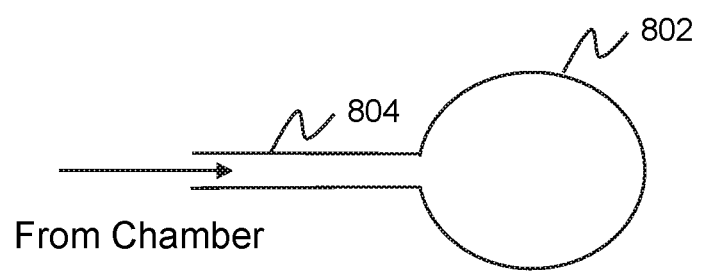
FIGS. 9A and 9B are schematic diagrams illustrating the pressure adjustment apparatus of FIG. 8 under exemplary pressure equalization statuses according to some embodiments of the present disclosure.
Figure 9B:
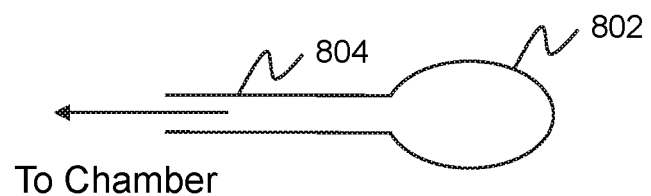

FIGS. 9A and 9B are schematic diagrams illustrating the pressure adjustment apparatus of FIG. 8 under exemplary pressure equalization statuses according to some embodiments of the present disclosure. In some embodiments, under an initial pressure equalization status of the pressure adjustment apparatus 800 as shown in FIG. 8, the first pressure may be equal to the second pressure, and the enclosure 802 may remain stationary. If the first pressure is equal to the second pressure, the enclosure 802 may remain stationary.

As shown in FIG. 9A, if the first pressure is larger than the second pressure (e.g., the first pressure increases and/or the second pressure decreases from the initial pressure equalization status or a previous pressure equalization status), the pressure difference between the first pressure and the second pressure may force the enclosure 802 to distort (e.g., expand), and the volume of the enclosure 802 may increase. Therefore, a portion of the radiation sensitive material may flow from the chamber volume to the enclosure 802 through the tube 804, the volume of the radiation sensitive material may increase, and the first pressure may reduce. In some embodiments, the enclosure 802 may be forced to distort until the first pressure is equalized with the second pressure. If the first pressure and the second pressure are equalized again, the distortion of the enclosure 802 may stop.

As shown in FIG. 9B, if the first pressure is lower than the second pressure (e.g., the first pressure decreases and/or the second pressure increases from the initial pressure equalization status or a previous pressure equalization status), the pressure difference between the first pressure and the second pressure may force the enclosure 802 to distort (e.g., shrink), and the volume of the enclosure 802 may be decreased. Therefore, a portion of the radiation sensitive material may flow from the enclosure 802 to the chamber volume through the tube 804, the volume of the radiation sensitive material may be decreased, and the first pressure may increase. In some embodiments, the enclosure 802 may be forced to distort until the first pressure is equalized with the second pressure. If the first pressure and the second pressure are equalized again, the distortion of the enclosure 802 may stop.

Figure 10:
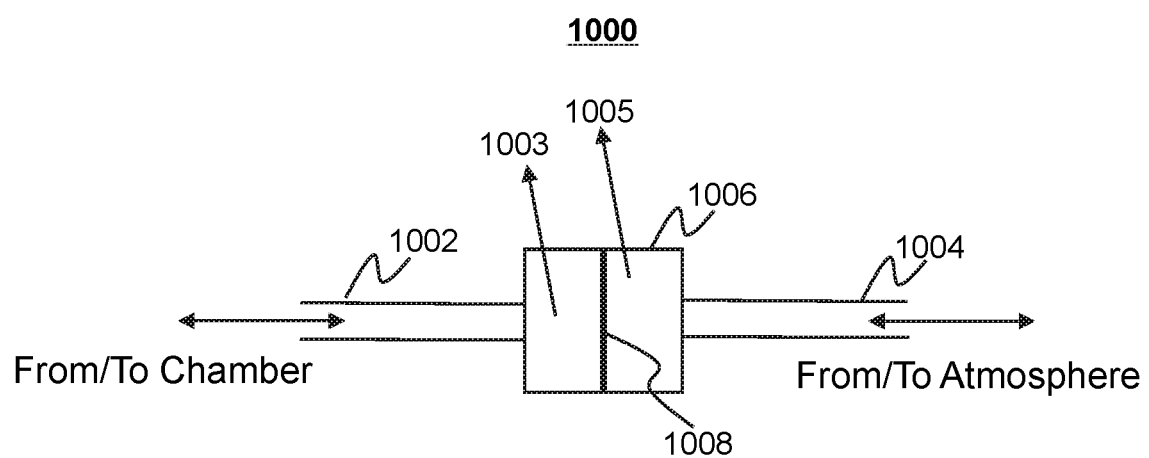
FIG. 10 is a schematic diagram illustrating another exemplary pressure adjustment apparatus according to some embodiments of the present disclosure.

FIG. 10 is a schematic diagram illustrating another exemplary pressure adjustment apparatus according to some embodiments of the present disclosure. As shown in FIG. 10, the pressure adjustment apparatus 1000 may include an enclosure 1006, and a pressure regulating element 1008. In some embodiments, the enclosure 1006 may be configured to function as a reservoir of the radiation sensitive material. In some embodiments, the pressure regulating element 1008 may separate the enclosure 1006 into a first space 1003 and a second space 1005. In some embodiments, the first space 1003 may be in fluid communication with the chamber volume via a tube 1002. In some embodiments, the second space 1005 may be in fluid communication with the ambient air (e.g., via another tube 1004). In some embodiments, the tube 1004 may be omitted.

In some embodiments, the pressure regulating element 1008 may be configured to equalize the first pressure and the second pressure by regulating a first size (e.g., volume) of the first space 1003 and a second size (e.g., volume) of the second space 1005. In some embodiments, the pressure regulating element 1008 may be a flexible membrane, a moveable membrane, a plunger, or a concertina, or the like.

Exemplary flexible membrane may include a polyethylene (PE) membrane, a polytetrafluoroethylene (PTFE) membrane, a polyurethane (PU) membrane, rubber, silica gel, elastic metal (such as nickel, titanium, stainless steel, etc.), or other suitable elastomer materials, or the like. In some embodiments, the moveable membrane may be flexible or rigid. A motion of the membrane may refer to a flexion, a displacement, a deflection, or any variation in the shape, position, orientation, and/or angle of the membrane or a portion of the membrane.

In some embodiments, the enclosure 1006 may be rigid. In some embodiments, the enclosure 1006 may be implemented in the configuration of a stainless steel tank, a glass bottle, or the like. In some embodiments, the enclosure 1006 may be of any suitable shape, such as a sphere shape, a column shape, a taper shape, or the like, or any combination thereof. In some embodiments, the enclosure 1006 may be airtightly and operably connected to the tube 1002 and/or the tube 1004. The pressure regulating element 1008 may be airtightly coupled to an inner wall of the enclosure 1006. For example, the pressure regulating element 1008 may be fixed to the inner wall of the enclosure 1006 through, for example, a threaded connection, a welded connection, a bell-and-spigot connection, a bonding connection, a fusion connection, or the like, or any combination thereof. In some embodiments, the pressure regulating element 1008 may be nonpermeable for the radiation sensitive material and the ambient air.

In some embodiments, the tube 1002 may include a first end and a second end. The first end may be open to the chamber volume, and the second end may be open to the enclosure 1006. In some embodiments, the first space 1003 of the enclosure 1006 may be in fluid communication with the chamber volume through the tube 1002. In some embodiments, at least one wall of the chamber housing may include a hole, and the first end of the tube 1002 may be airtightly connected to the at least one wall except for the hole. In some embodiments, the first end of the tube 1002 may be directly connected to the at least one wall. In some embodiments, the first end of the tube 1002 may be connected to the at least one wall through a connecting piece. In some embodiments, the first space 1003 of the enclosure 1006 and the tube 1002 may be airtight such that the radiation sensitive material inside the chamber volume, the first space 1003, and the tube 1002 may be isolated from the ambient air. In some embodiments, the tube 1002 may be made of a material including for example, a non-metallic material (e.g., plastic, glass, ceramics, rubber, silicon dioxide, silica gel, flexible quartz, or the like), a metallic material (e.g., copper, lead, iron, steel, silver, gold, chromium, rare-earth metal, or the like), or an alloy thereof, or any combination thereof. In some embodiments, the tube 1002 may have a uniform size and/or shape along an axis of the tube 1002. For example, the tube 1002 may be cylindrical of a diameter (e.g., 1 millimeter). In some embodiments, the tube 1002 may have a varying size and/or shape along the axis of the tube 1002. For example, the tube 1002 may have a substantially conical shape. As another example, a cross section of one end of the tube 1002 may have a circular shape (e.g., with a diameter of 1 millimeter), while a cross section of another end of the tube 1002 may have a hexagon shape (e.g., each side of which is 0.5 millimeters long). In some embodiments, the material, the size, and/or the shape of the tube 1004 may be the same as or different from those of the tube 1002.

In some embodiments, if the first pressure is equal to the second pressure, the pressure regulating element 1008 may remain stationary (e.g., the pressure regulating element 1008 may have no distortion, the pressure regulating element 1008 may be in a middle position inside the enclosure 1006, or the like). In some embodiments, if the first pressure becomes different from the second pressure, a pressure difference between the first pressure and the second pressure may force the pressure regulating element 1008 to distort, and/or move. For example, if the pressure regulating element 1008 is a flexible membrane or a concertina, the pressure regulating element 1008 may distort because of the pressure difference between the first pressure and the second pressure. As another example, if the pressure regulating element 1008 is a plunger, the pressure regulating element 1008 may move (or the position of the pressure regulating element 1008 may change) because of the pressure difference between the first pressure and the second pressure. Accordingly, the volume of the first space 1003 and the second space 1005 may change, and the first pressure can be adjusted. More descriptions of the pressure equalization may be found elsewhere in the present disclosure (e.g., FIGS. 11A and 11B and descriptions thereof).

Figure 11A:
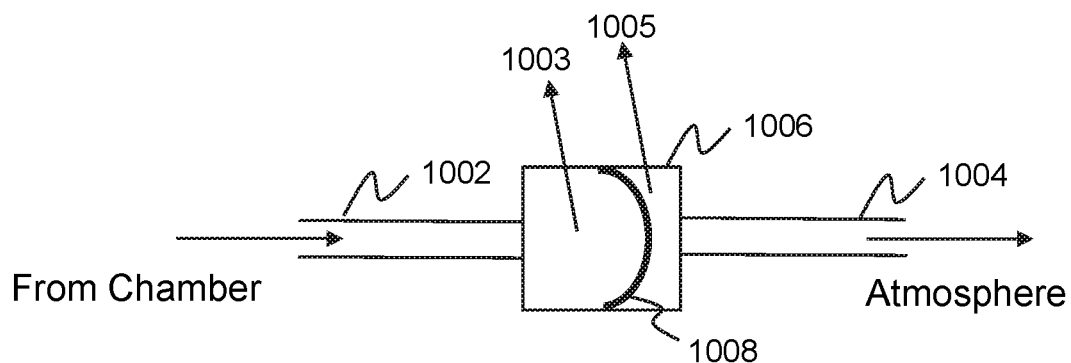
FIGS. 11A and 11B are schematic diagrams illustrating the pressure adjustment apparatus of FIG. 10 under exemplary pressure equalization statuses according to some embodiments of the present disclosure.
Figure 11B:
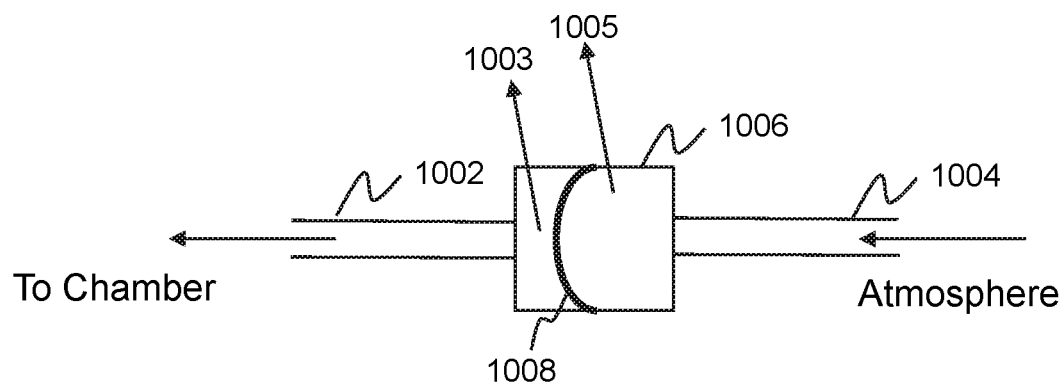

FIGS. 11A and 11B are schematic diagrams illustrating the pressure adjustment apparatus of FIG. 10 under exemplary pressure equalization statuses according to some embodiments of the present disclosure.

As shown in FIG. 11A, if the first pressure is larger than the second pressure (e.g., the first pressure increases and/or the second pressure decreases from the initial pressure equalization status or a previous pressure equalization status), the pressure difference between the first pressure and the second pressure may force the pressure regulating element 1008 to distort (e.g., protrude towards the second space 1005) or move (e.g., towards the second space 1005), and the volume of the first space 1003 may increase. Therefore, a portion of the radiation sensitive material may flow from the chamber volume to the first space 1003 through the tube 1002, the volume of the radiation sensitive material may increase, and the first pressure may reduce. In some embodiments, the pressure regulating element 1008 may be forced to distort or move until the first pressure is equalized with the second pressure. If the first pressure and the second pressure are equalized again, the distortion or movement of the pressure regulating element 1008 may stop.

As shown in FIG. 11B, if the first pressure is lower than the second pressure (e.g., the first pressure decreases and/or the second pressure increases from the initial pressure equalization status or a previous pressure equalization status), the pressure difference between the first pressure and the second pressure may force the pressure regulating element 1008 to distort (e.g., protrude towards the first space 1003) or move (e.g., towards the first space 1003), and the volume of the first space 1003 may be decreased. Therefore, a portion of the radiation sensitive material may flow from the first space 1003 to the chamber volume through the tube 1002, the volume of the radiation sensitive material may be decreased, and the first pressure may increase. In some embodiments, the pressure regulating element 1008 may be forced to distort or move until the first pressure is equalized with the second pressure. If the first pressure and the second pressure are equalized again, the distortion or movement of the pressure regulating element 1008 may stop.

Figure 12:
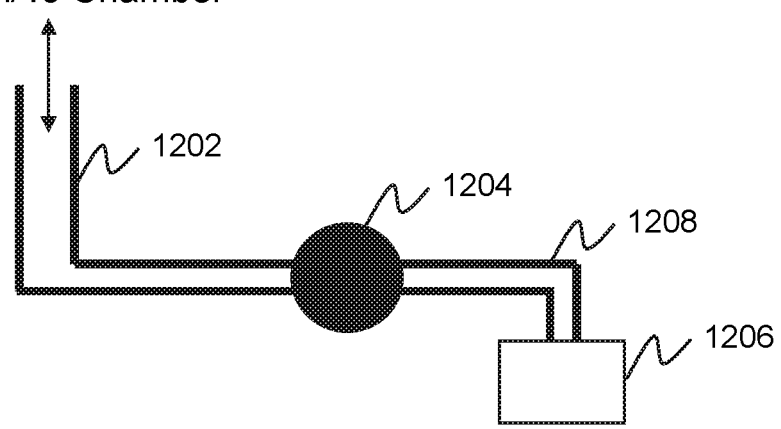
FIG. 12 is a schematic diagram illustrating another exemplary pressure adjustment apparatus according to some embodiments of the present disclosure.

FIG. 12 is a schematic diagram illustrating another exemplary pressure adjustment apparatus according to some embodiments of the present disclosure. As shown in FIG. 12, the pressure adjustment apparatus 1200 may include an enclosure 1206 and a pump 1204. In some embodiments, the enclosure 1206 may be configured to function as a reservoir of the radiation sensitive material that is the same as that in the ionization chamber. In some embodiments, the enclosure 1206 may include a flexible enclosure, such as a balloon, a bellow, or the like. In some embodiments, the enclosure 1206 may include a rigid enclosure, such as a stainless steel tank, a glass bottle, or the like. In some embodiments, the enclosure 1206 may be replaceable. For example, if the amount of the radiation sensitive material in the enclosure 1206 is less than a threshold value, and/or the enclosure 1206 fails to equalize the first pressure and the second pressure, the enclosure 1206 may be replaced by another enclosure with sufficient amount of radiation sensitive material. In some embodiments, the enclosure 1206 may be operably coupled to another reservoir of the radiation sensitive material (or a secondary reservoir of the radiation sensitive material). In some embodiments, if the amount of the radiation sensitive material in the enclosure 1206 is less than a first threshold value, the secondary reservoir may provide radiation sensitive material for the enclosure 1206 for storing. In some embodiments, if the amount of the radiation sensitive material in the enclosure 1206 is larger than a second threshold value, the enclosure 1206 may provide radiation sensitive material for the secondary reservoir for storing. In some embodiments, the enclosure 1206 may be of any suitable shape, such as a sphere shape, a column shape, a taper shape, or the like, or any combination thereof.

In some embodiments, the pump 1204 may be configured to pump, based on the first pressure and the second pressure, the radiation sensitive material to flow between the enclosure 1206 and the chamber volume. For example, if the first pressure is less than the second pressure, the pump 1204 may pump the radiation sensitive material from the enclosure 1206 into the chamber volume of the ionization chamber to equalize the first pressure and the second pressure. As another example, if the first pressure is larger than the second pressure, the pump 1204 may pump the radiation sensitive material from the chamber volume of the ionization chamber into the enclosure 1206 to equalize the first pressure and the second pressure. In some embodiments, the pump 1204 may include a piezoelectric air pump, a vane pump, a diaphragm pump, a drum pump, a centrifugal pump, a reciprocation pump, a vacuum pump, or the like. In some embodiments, the pump 1204 may be reversible. A reversible pump may refer that a direction of rotation of the pump can be reversible, or the reversible pump may make the radiation sensitive material flow from the enclosure 1206 to the chamber volume and from the chamber volume to the enclosure 1206 according to situations. For example, as shown in FIG. 12, the pump 1204 may pump the radiation sensitive material from the chamber volume of the ionization chamber into the enclosure 1206 when the first pressure is larger than the second pressure, and pump the radiation sensitive material from the enclosure 1206 into the chamber volume of the ionization chamber when the first pressure is lower than the second pressure.

In some embodiments, the enclosure 1206 may be in fluid communication with the chamber volume via one or more tubes (e.g., a tube 1202, a tube 1208). In some embodiments, the enclosure 1206 and the tube(s) may be airtight such that the radiation sensitive material inside the chamber volume, the enclosure 1206, and the tube(s) is isolated from the ambient air. As illustrated in FIG. 12, the tube 1202 and the tube 1208 may be implemented in the configuration of a single tube or two independent tubes. In some embodiments, the pump 1204 may be operably coupled to the tube(s) between the chamber volume and the enclosure 1206.

In some embodiments, the tube 1202 may include a first end and a second end. The first end may be open to the chamber volume, and the second end may be open to the pump 1204 or the enclosure 1206. In some embodiments, the enclosure 1006 may be in fluid communication with the chamber volume through the tube 1202. In some embodiments, at least one wall of the chamber housing may include a hole, and the first end of the tube 1202 may be airtightly connected to the at least one wall except for the hole. In some embodiments, the first end of the tube 1202 may be directly connected to the at least one wall. In some embodiments, the first end of the tube 1202 may be connected to the at least one wall through a connecting piece. In some embodiments, the tube 1202 may be made of a material including for example, a non-metallic material (e.g., plastic, glass, ceramics, rubber, silicon dioxide, silica gel, flexible quartz, or the like), a metallic material (e.g., copper, lead, iron, steel, silver, gold, chromium, rare-earth metal, or the like), or an alloy thereof, or any combination thereof. In some embodiments, the tube 1202 may have a uniform size and/or shape along an axis of the tube 1202. For example, the tube 1202 may be cylindrical of a diameter (e.g., 1 millimeter). In some embodiments, the tube 1202 may have a varying size and/or shape along the axis of the tube 1202. For example, the tube 1202 may have a substantially conical shape. As another example, a cross section of one end of the tube 1202 may have a circular shape (e.g., with a diameter of 1 millimeter), while a cross section of another end of the tube 1202 may have a hexagon shape (e.g., each side of which is 0.5 millimeters long). In some embodiments, the material, the size, and/or the shape of the tube 1208 may be the same as or different from those of the tube 1202.

In some embodiments, the pressure adjustment apparatus 1200 may include one or more sensors (e.g., pressure sensors). The pressure sensor(s) may be configured to detect a pressure of the radiation sensitive material inside the chamber volume and/or the pressure adjustment apparatus 1200 (e.g., the first pressure), and/or a pressure of the ambient air outside the chamber housing (e.g., the second pressure). For example, the pressure adjustment apparatus 1200 may be equipped with a first pressure sensor configured to detect the first pressure, and a second pressure sensor configured to detect the second pressure. Exemplary pressure sensors may include a strain pressure sensor, a piezoresistive pressure sensor, a capacitive pressure sensor, a piezoelectric pressure sensor, an inductance pressure sensor, or the like, or any combination thereof. In some embodiments, the first pressure sensor may be operably coupled to the tube 1202. In some embodiments, the second pressure sensor may be operably coupled to an outer surface of the pressure adjustment apparatus 1200 to detect the second pressure. In some embodiments, the second pressure sensor may not be coupled to the pressure adjustment apparatus 1200, and may be positioned at a distance away from the pressure adjustment apparatus 1200. The second pressure sensor may send data or information of the second pressure to the pressure adjustment apparatus 1200 or the processing device 140 via the network 120.

In some embodiments, the pump 1204 may be controlled by a controller. In some embodiments, the controller may obtain the pressure information detected by the pressure sensor(s) (e.g., the first pressure and the second pressure), and control the pump 1204 to operate based on the pressure information. In some embodiments, the controller may be integrated into the pump 1204. In some embodiments, the controller may be integrated into the processing device 140, and thus, the processing device 140 may obtain the pressure information, transmit instruction(s) to the pump 1204, and/or control the operation of the pump 1204. In some embodiments, if the first pressure is equal to the second pressure, the pump 1204 may be in a standby state or off state (or inactive state), and the pump 1204 may block a fluid communication between the chamber volume and the enclosure 1206. In some embodiments, if the first pressure becomes different from the second pressure, the pump 1204 may pump the radiation sensitive material to flow between the enclosure 1206 and the chamber volume. Although the volume of the radiation sensitive material in the chamber volume may be unchanged, the amount of the radiation sensitive material in the chamber volume may change, and thus, the first pressure can be adjusted to be equalized with the second pressure.

Figure 13:
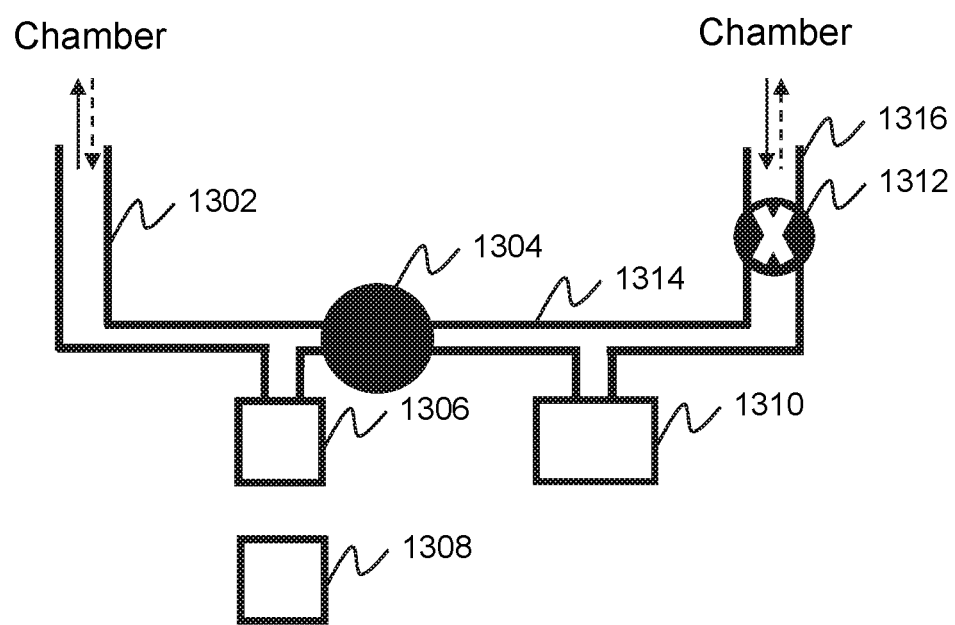
FIG. 13 is a schematic diagram illustrating another exemplary pressure adjustment apparatus according to some embodiments of the present disclosure.

FIG. 13 is a schematic diagram illustrating another exemplary pressure adjustment apparatus according to some embodiments of the present disclosure. As shown in FIG. 13, the pressure adjustment apparatus 1300 may include an enclosure 1310, and a pump 1304. In some embodiments, the enclosure 1310 may be configured to function as a reservoir of the radiation sensitive material that is the same as that in the ionization chamber. In some embodiments, the configuration of the enclosure 1310 may be the same as the configuration of the enclosure 1206 illustrated in FIG. 12. More descriptions of the enclosure may be found elsewhere in the present disclosure (e.g., FIG. 12 and descriptions thereof).

In some embodiments, the pressure adjustment apparatus 1300 may further include one or more tubes, for example, the tube 1302, the tube 1314, and/or the tube 1316. In some embodiments, the tube(s) may be implemented in the configuration of a single tube or two independent tubes. For example, the tube 1302, the tube 1314, and the tube 1316 may be configured as a single tube, and the tube may include a first end and a second end. The tube may guide the radiation sensitive material to flow into and out of the chamber volume. The first end and the second end of the tube may be in fluid communication with the chamber volume. The first end of the tube may be operably coupled to (e.g., airtightly connected to) a first location of the chamber housing, and the second end of the tube may be operably coupled to (e.g., airtightly connected to) a second location of the chamber housing. The first location may be different from the second location. In some embodiments, the first end and/or the second end of the tube may be directly connected to the wall(s) of the chamber housing (e.g., via a first hole and a second hole of the wall(s), respectively). In some embodiments, the first end and/or the second end of the tube may be connected to the wall(s) of the chamber housing through a connecting piece. In some embodiments, the pump 1304 may be operably coupled to a portion of the tube. In some embodiments, the enclosure 1310 may be operably connected to the tube and in fluid communication with the tube. In some embodiments, the enclosure 1310 and the tube may be airtight such that the radiation sensitive material inside the enclosure and the tube is isolated from the ambient air.

Alternatively, in some embodiments, the tube 1302, the tube 1314, and the tube 1316 may be configured as separate tubes. A first end of the tube 1302 may be open to the chamber volume. In some embodiments, at least one wall of the chamber housing may include a first hole, and the first end of the tube 1302 may be airtightly connected to the at least one wall via the first hole. A second end of the tube 1302 may be operably connected to the pump 1304. A first end of the tube 1314 may be operably connected to the pump 1304. A second end of the tube 1314 may be operably connected to a valve 1312. A first end of the tube 1316 may be operably connected to the valve 1312. A second end of the tube 1316 may be open to the chamber volume. In some embodiments, at least one wall of the chamber housing may include a second hole, and the second end of the tube 1316 may be airtightly connected to the at least one wall via the second hole. In some embodiments, the first end of the tube 1302 and/or the second end of the tube 1316 may be directly connected to the wall(s) of the chamber housing (e.g., via the first hole and the second hole of the wall(s), respectively). In some embodiments, the first end of the tube 1302 and/or the second end of the tube 1316 may be connected to the wall(s) of the chamber housing through a connecting piece. In some embodiments, the enclosure 1310 may be operably connected to the tube 1314 and in fluid communication with the tube 1314. In some embodiments, the enclosure 1310, the tube 1302, the tube 1316, and the tube 1314 may be airtight such that the radiation sensitive material inside the enclosure 1310 and the tubes is isolated from the ambient air. In some embodiments, the fluid communication between the tube 1302 and the tube 1314 may be controlled by the pump 1304. For example, the on/off state of the fluid communication between the tube 1302 and the tube 1314, the flow rate and/or the flow direction of the radiation sensitive material between the tube 1302 and the tube 1314 may be controlled by the pump 1304. In some embodiments, the fluid communication between the tube 1314 and the tube 1316 may be controlled by the valve 1312. For example, the on/off state of the fluid communication between the tube 1316 and the tube 1314, the flow rate of the radiation sensitive material between the tube 1316 and the tube 1314 may be controlled by the valve 1312.

In some embodiments, the tube 1302 may be made of a material including for example, a non-metallic material (e.g., plastic, glass, ceramics, rubber, silicon dioxide, silica gel, flexible quartz, or the like), a metallic material (e.g., copper, lead, iron, steel, silver, gold, chromium, rare-earth metal, or the like), or an alloy thereof, or any combination thereof. In some embodiments, the tube 1302 may have a uniform size and/or shape along an axis of the tube 1302. For example, the tube 1302 may be cylindrical of a diameter (e.g., 1 millimeter). In some embodiments, the tube 1302 may have a varying size and/or shape along the axis of the tube 1302. For example, the tube 1302 may have a substantially conical shape. As another example, a cross section of one end of the tube 1302 may have a circular shape (e.g., with a diameter of 1 millimeter), while a cross section of another end of the tube 1302 may have a hexagon shape (e.g., each side of which is 0.5 millimeters long). In some embodiments, the material, the size, and/or the shape of the tube 1314 and or the tube 1316 may be the same as or different from those of the tube 1002.

In some embodiments, similar to the pressure adjustment apparatus 1200 illustrated in FIG. 12, the pump 1304 may be configured to pump, based on the first pressure and the second pressure, the radiation sensitive material to flow between the enclosure 1310 and the chamber volume via the tube(s). For example, if the first pressure is less than the second pressure, the pump 1304 may pump the radiation sensitive material from the enclosure 1310 into the chamber volume of the ionization chamber to equalize the first pressure and the second pressure. As another example, if the first pressure is larger than the second pressure, the pump 1304 may pump the radiation sensitive material from the chamber volume of the ionization chamber into the enclosure 1310 to equalize the first pressure and the second pressure. In some embodiments, the pump 1304 may include a piezoelectric air pump (such as Murata Microblower), a vane pump, a diaphragm pump, a drum pump, a centrifugal pump, a reciprocation pump, a vacuum pump, or the like. In some embodiments, the pump 1304 may be reversible. For example, as shown in FIG. 13, the pump 1304 may pump the radiation sensitive material from the chamber volume of the ionization chamber into the enclosure 1310 and pump the radiation sensitive material from the enclosure 1310 into the chamber volume of the ionization chamber. In some embodiments, the pump 1304 may be irreversible. For example, the pump 1304 may only allow the radiation sensitive material to flow from the tube 1302 into the tube 1314. As another example, the pump 1304 may only allow the radiation sensitive material to flow from the tube 1314 into the tube 1302.

In some embodiments, the pressure adjustment apparatus 1300 may include one or more sensors (e.g., pressure sensors, temperature sensors, etc.). The pressure sensor(s) may be configured to detect a pressure of the radiation sensitive material inside the chamber volume and/or the pressure adjustment apparatus 1300 (e.g., the first pressure), and/or a pressure of the ambient air outside the chamber housing (e.g., the second pressure). For example, the pressure adjustment apparatus 1300 may be equipped with a first pressure sensor 1306 configured to detect the first pressure (e.g., by detecting a pressure of the radiation sensitive material flowing through the tube(s)), and a second pressure sensor 1308 configured to detect the second pressure. Exemplary pressure sensors may include a strain pressure sensor, a piezoresistive pressure sensor, a capacitive pressure sensor, a piezoelectric pressure sensor, an inductance pressure sensor, or the like, or any combination thereof. In some embodiments, the first pressure sensor 1306 may be operably coupled to the tube 1302, the tube 1314, and/or the tube 1316. In some embodiments, the second pressure sensor 1308 may be operably coupled to an outer surface of the pressure adjustment apparatus 1300 to detect the second pressure. In some embodiments, the second pressure sensor 1308 may not be coupled to the pressure adjustment apparatus 1300 and may be positioned at a distance away from the pressure adjustment apparatus 1300. The second pressure sensor 1308 may send data or information of the second pressure to the pressure adjustment apparatus 1300 or the processing device 140 via the network 120. The temperature sensor(s) (or thermometer) may be configured to detect a temperature of the radiation sensitive material inside the chamber volume (e.g., by detecting a temperature of the radiation sensitive material flowing through the tube(s). In some embodiments, the temperature sensor(s) may be operably coupled to the tube 1302, the tube 1314, and/or the tube 1316. In some embodiments, because the temperature of the radiation sensitive material may be influential on the density of the radiation sensitive material and/or the first pressure, the detected temperature of the radiation sensitive material may be used to compensate the detected intensity of radiation beams.

In some embodiments, the pump 1304 may be configured to pump continuously the radiation sensitive material to flow between the chamber volume and the tube(s). For example, the pump 1304 may pump continuously the radiation sensitive material to flow from the chamber volume, to the tube 1302, the tube 1314, and the tube 1316 sequentially, and back to the chamber volume, as indicated by the dashed arrows in FIG. 13. As another example, the pump 1304 may pump continuously the radiation sensitive material to flow from the chamber volume, to the tube 1316, the tube 1314, and the tube 1302 sequentially, and back to the chamber volume, as indicated by the solid arrows in FIG. 13. Because the radiation sensitive material are circulated between the chamber volume and the tube(s), the temperature and/or the pressure of the radiation sensitive material detected by the sensors coupled to the tube(s) can be substantially the same as the temperature and/or the pressure of the radiation sensitive material inside the chamber volume.

In some embodiments, the valve 1312 may be configured to adjust a quantity (or flux) of the radiation sensitive material flowing, through the tube 1316, in or out of the chamber volume. The valve 1312 may include a proportional valve. In some embodiments, if the flow speed of the radiation sensitive material controlled by the pump 1304 is not sufficient to equalize the first pressure and the second pressure, or the pump 1304 is irreversible, the valve 1312 may adjust the quantity of the radiation sensitive material that flows through the valve 1312 to facilitate the equalization of the first pressure and the second pressure.

In some embodiments, the pump 1304 and/or the valve 1312 may be controlled by a controller. In some embodiments, the controller may obtain the pressure and/or temperature information detected by the sensor(s) (e.g., the first pressure and the second pressure), and control the pump 1304 and/or the valve 1312 to operate based on the pressure and/or temperature information. In some embodiments, the controller may be integrated into the pump 1304 and/or the valve 1312. In some embodiments, the controller may be integrated into the processing device 140, and thus, the processing device 140 may obtain the pressure and/or temperature information, transmit instruction(s) to the pump 1304 and/or the valve 1312, and/or control the operation of the pump 1304 and/or the valve 1312. In some embodiments, if the first pressure is equal to the second pressure, the pump 1304 may pump continuously the radiation sensitive material to flow (e.g., in a steady speed) between the chamber volume and the tube(s). In some embodiments, if the first pressure becomes different from the second pressure, the pump 1304 may pump the radiation sensitive material to flow between the enclosure 1310 and the chamber volume, and/or between the chamber volume and the tube(s). For example, if the first pressure is lower than the second pressure, the pump 1304 and/or the valve 1312 may be controlled to cause the radiation sensitive material to flow from the enclosure 1310 into the chamber volume via the tube(s). As another example, if the first pressure is larger than the second pressure, the pump 1304 and/or the valve 1312 may be controlled to cause the radiation sensitive material to flow from the chamber volume into the enclosure 1310 via the tube(s). Although the volume of the radiation sensitive material in the chamber volume may be unchanged, the amount of the radiation sensitive material in the chamber volume may change, and thus, the first pressure can be adjusted to be equalized with the second pressure.

Figure 14:
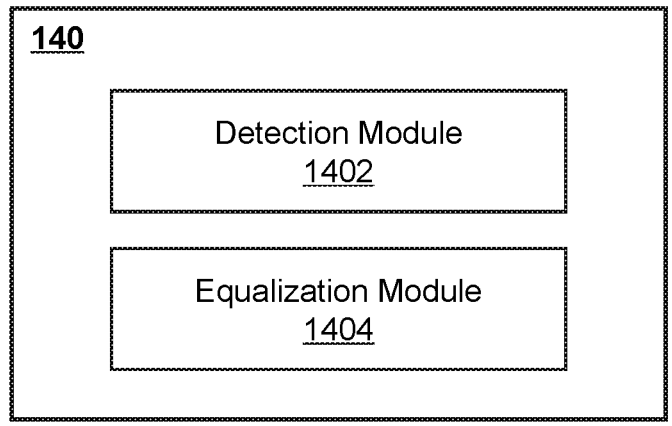
FIG. 14 is a block diagram illustrating an exemplary processing device according to some embodiments of the present disclosure.

FIG. 14 is a block diagram illustrating an exemplary processing device according to some embodiments of the present disclosure. In FIG. 14, the processing device 140 may include a detection module 1402, and an equalization module 1404.

The detection module 1402 may be configured to detect a first pressure of a radiation sensitive material inside an ionization chamber, and/or a second pressure of an atmosphere air outside the ionization chamber. In some embodiments, the detection module 1402 may include a first pressure sensor configured to detect the first pressure. In some embodiments, the detection module 1402 may include a second pressure sensor configured to detect the second pressure. The first pressure sensor and the second pressure sensor may be of the same type or different types. More descriptions of the first pressure sensor, the second pressure sensor, and the detection of the first pressure and the second pressure may be found elsewhere in the present disclosure (e.g., FIGS. 12-13, and 15, and descriptions thereof).

The equalization module 1404 may be configured to equalize the first pressure and the second pressure. In some embodiments, the equalization module 1404 may equalize the first pressure and the second pressure, e.g., by by pumping, using a pump, the radiation sensitive material to flow between a reservoir of the radiation sensitive material (e.g., the enclosure 1206, the enclosure 1310) and the ionization chamber. More descriptions of the equalization of the first pressure and the second pressure may be found elsewhere in the present disclosure (e.g., FIGS. 12-13, and 15, and descriptions thereof).

Figure 15:
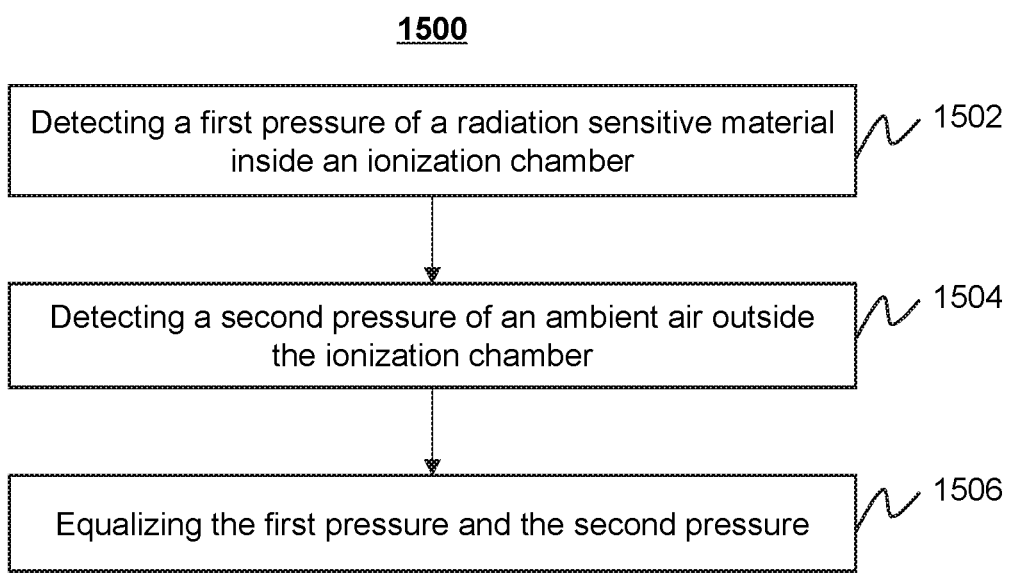
FIG. 15 is a flowchart illustrating an exemplary pressure adjustment process according to some embodiments of the present disclosure.

FIG. 15 is a flowchart illustrating an exemplary pressure adjustment process according to some embodiments of the present disclosure. In some embodiments, the process 1500 may be executed by the radiation system 100. For example, the process 1500 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 1500 presented below are intended to be illustrative. In some embodiments, the process may be accomplished with one or more additional operations not described, and/or without one or more of the operations discussed. Additionally, the order in which the operations of the process 1500 as illustrated in FIG. 15 and described below is not intended to be limiting.

In some embodiments, an ionization chamber (e.g., the ionization chamber 400, the ionization chamber 500) may be provided. The ionization chamber may include a chamber housing including one or more chamber walls, a chamber volume inside the chamber housing, and a pressure adjustment apparatus (e.g., the pressure adjustment apparatus 1200, the pressure adjustment apparatus 1300) operably coupled to at least one wall of the one or more chamber walls. In some embodiments, the chamber volume may be filled with the radiation sensitive material. In some embodiments, the pressure adjustment apparatus may be operably coupled to at least one wall of the one or more chamber walls. The pressure adjustment apparatus may be configured to equalize a first pressure of the radiation sensitive material inside the chamber volume and a second pressure of the ambient air outside the chamber housing.

In 1502, a first pressure of a radiation sensitive material inside an ionization chamber may be detected. In some embodiments, the processing device 140 (e.g., the detection module 1402) may perform operation 1502. In some embodiments, the first pressure of the radiation sensitive material may be detected by a first pressure sensor. In some embodiments, the first pressure may be transmitted from the first pressure sensor to the processing device 140, and the processing device 140 may obtain the first pressure. In some embodiments, the processing device 140 may transmit an instruction to the first pressure sensor to detect the first pressure. More descriptions of the first pressure sensor and the detection of the first pressure may be found elsewhere in the present disclosure (e.g., FIGS. 12-13 and descriptions thereof).

In 1504, a second pressure of an atmosphere air outside the ionization chamber may be detected. In some embodiments, the processing device 140 (e.g., the detection module 1402) may perform operation 1504. In some embodiments, the second pressure of the atmosphere air outside the ionization chamber may be detected by a second pressure sensor. The first pressure sensor and the second pressure sensor may be of the same type or different types. In some embodiments, the second pressure may be transmitted from the second pressure sensor to the processing device 140, and the processing device 140 may obtain the second pressure. In some embodiments, the processing device 140 may transmit an instruction to the second pressure sensor to detect the second pressure. More descriptions of the second sensor and the detection of the second pressure may be found elsewhere in the present disclosure (e.g., FIGS. 12-13 and descriptions thereof).

In 1506, the first pressure and the second pressure may be equalized. In some embodiments, the processing device 140 (e.g., the equalization module 1404) may perform operation 1506. In some embodiments, the processing device 140 may equalize the first pressure and the second pressure, e.g., by pumping, using a pump, the radiation sensitive material to flow between a reservoir of the radiation sensitive material (e.g., the enclosure 1206, the enclosure 1310) and the ionization chamber. In some embodiments, the processing device 140 (e.g., the equalization module 1404) may compare the first pressure and the second pressure. In some embodiments, in response to a determination that the first pressure is larger than the second pressure, the processing device 140 may control the pump to pump the radiation sensitive material from the ionization chamber to the reservoir. In some embodiments, in response to a determination that the second pressure is larger than the first pressure, the processing device 140 may control the pump to pump the radiation sensitive material from the reservoir to the ionization chamber.

In some embodiments, the processing device 140 may further allow the radiation sensitive material to flow between the ionization chamber and one or more tube(s) operably coupled to the ionization chamber (see FIG. 13). In some embodiments, in 1502, the processing device 140 may detect the first pressure of the radiation sensitive material inside the ionization chamber by detecting a pressure of the radiation sensitive material flowing through the tube(s). In some embodiments, the processing device 140 may control the pump to pump continuously the radiation sensitive material inside the tube(s) into the ionization chamber, and/or pump continuously the radiation sensitive material from the ionization chamber into the tube(s). In some embodiments, the processing device 140 may compare the first pressure and the second pressure. In some embodiments, in response to a determination that the first pressure is different from the second pressure and that a pumping direction of the pump is irreversible, the processing device 140 may adjust a proportional valve (e.g., the valve 1312 in FIG. 13) (e.g., adjust a quantity (or flux) of the radiation sensitive material flowing, through the tube(s), in or out of the chamber volume) to equalize the first pressure and the second pressure. In some embodiments, the processing device 140 may compare a pump speed of the pump and a threshold. In some embodiments, in response to a determination that the first pressure is different from the second pressure and that the pump speed of the pump is no less than the threshold, the processing device 140 may adjust the proportional valve to equalize the first pressure and the second pressure.

It should be noted that the above description of the process 1500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1502 and 1504 may be integrated into a single operation. As another example, operation 1506 may be divide into a comparison operation and an equalization operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A hybrid of a sealed and unsealed ionization chamber, comprising:
   a chamber housing including one or more chamber walls, each of the one or more chamber walls having a thin thickness between 10 micrometers and 2 millimeters to facilitate detection of radiation beams by lowering an amount of attenuation experienced by the radiation beams due to transition through the one or more chamber walls;
   a chamber volume inside the chamber housing, the chamber volume being filled with a radiation sensitive material and being on the path of the radiation beams;
   one or more electrodes configured to establish an electric field in the chamber volume and measure a charge or current associated with the radiation sensitive material and produced, based on the electric field, in the chamber volume; and
   a pressure adjustment apparatus operably coupled to the chamber volume via at least one wall of the one or more chamber walls, wherein the at least one wall includes a hole so that the chamber volume is in fluid communication with the pressure adjustment apparatus, the pressure adjustment apparatus being configured to equalize a first pressure of the radiation sensitive material inside the chamber volume relative to a second pressure of ambient air outside the chamber housing, the second pressure being influenced by at least one of temperature variation, pressure variation, or moisture variation in the ambient air, the pressure adjustment apparatus including a tube and an enclosure configured to function as a reservoir of the radiation sensitive material, wherein
   the enclosure is connected to the chamber volume by the tube; and
   the enclosure is configured to prevent the chamber volume from being in fluid communication with the ambient air and be nonpermeable for the radiation sensitive material and the ambient air.

2. The ionization chamber of claim 1, wherein the chamber volume is airtight.

3. The ionization chamber of claim 1, wherein the radiation sensitive material includes a gas.

4. The ionization chamber of claim 1, wherein
   the tube includes a first end and a second end, the first end being open to the chamber volume, and the second end being open to the enclosure; and the tube has a varying size and/or shape along an axis of the tube.

5. The ionization chamber of claim 4, wherein the at least one wall includes a hole, and the first end of the tube is airtightly connected to the at least one wall via the hole.

6. The ionization chamber of claim 4, wherein the first end of the tube is directly connected to the at least one wall.

7. The ionization chamber of claim 4, wherein the first end of the tube is connected to the at least one wall through a connecting piece.

8. The ionization chamber of claim 4, wherein the enclosure is in fluid communication with the chamber volume through the tube.

9. The ionization chamber of claim 4, wherein the enclosure and the tube are airtight such that the radiation sensitive material inside the enclosure and the tube is isolated from the ambient air.

10. The ionization chamber of claim 1, wherein the enclosure is flexible.

11. The ionization chamber of claim 10, wherein the enclosure includes a balloon, a bellows, or a flexible enclosure.

\* \* \* \* \*